(12) United States Patent
Almogy et al.

(10) Patent No.: US 9,075,909 B2
(45) Date of Patent: Jul. 7, 2015

(54) SYSTEM AND METHOD TO ENABLE DETECTION OF VIRAL INFECTION BY USERS OF ELECTRONIC COMMUNICATION DEVICES

(71) Applicants: Gal Almogy, Tel Aviv (IL); Gilad Almogy, Palo Alto, CA (US)

(72) Inventors: Gal Almogy, Tel Aviv (IL); Gilad Almogy, Palo Alto, CA (US)

(73) Assignee: FLURENSICS INC., Tel Aviv (IL)

( * ) Notice: Subject to any disclaimer, the term of this patent is extended or adjusted under 35 U.S.C. 154(b) by 274 days.

(21) Appl. No.: 13/680,289

(22) Filed: Nov. 19, 2012

(65) Prior Publication Data

US 2013/0318027 A1    Nov. 28, 2013

Related U.S. Application Data

(60) Provisional application No. 61/561,884, filed on Nov. 20, 2011.

(51) Int. Cl.
| | | |
|---|---|---|
| G06F 9/44 | (2006.01) | |
| G06N 7/02 | (2006.01) | |
| G06N 7/06 | (2006.01) | |
| G06F 19/00 | (2011.01) | |

(52) U.S. Cl.
CPC .......... *G06F 19/345* (2013.01); *G06F 19/3493* (2013.01)

(58) Field of Classification Search
USPC .......................................................... 706/52
See application file for complete search history.

(56) References Cited

U.S. PATENT DOCUMENTS

| | | | |
|---|---|---|---|
| 7,399,276 B1 | 7/2008 | Brown et al. | |
| 7,817,046 B2 | 10/2010 | Coveley et al. | |
| 7,840,421 B2 * | 11/2010 | Gerntholtz | 705/3 |
| 7,893,842 B2 * | 2/2011 | Deutsch | 340/573.1 |
| 7,940,174 B2 * | 5/2011 | Tuck | 340/539.13 |
| 8,144,007 B2 * | 3/2012 | Tuck et al. | 340/539.13 |
| 8,190,681 B2 * | 5/2012 | Markus et al. | 709/204 |
| 8,271,294 B2 | 9/2012 | Eisenberger et al. | |
| 8,412,706 B2 * | 4/2013 | McGuire et al. | 707/732 |

(Continued)

OTHER PUBLICATIONS

Modeling and evaluation of disease spread behaviors, Guizani, N. ; Ghafoor, A. Wireless Communications and Mobile Computing Conference (IWCMC), 2014 International DOI: 10.1109/IWCMC.2014. 6906491 Publication Year: 2014 , pp. 969-1003.*

(Continued)

*Primary Examiner* — Michael B Holmes
(74) *Attorney, Agent, or Firm* — Reches Patents

(57) ABSTRACT

A non-transitory computer readable medium that stores instructions for causing a computerized system to perform the following operations: determining, by the computerized system, that a first person is infected by a first infectious disease; wherein the determination is associated with a first person infection probability attribute; detecting, by the computerized system, based upon location information collected during at least a portion of a first infectious disease manifestation period, the location information being indicative of locations of the first person and other persons, a second person that was within an infection distance from the first person and is potentially infected by the first infectious disease; calculating, by the computerized system, a second person infection probability attribute; and updating, by the computerized system, the first person infection probability attribute in response to the second person infection probability attribute.

20 Claims, 19 Drawing Sheets

---

Modeling basic viral dynamics requires a "viral strategy"

The main public health danger is a rapidly spreading, highly pathogenic airborne (respiratory) infection reminiscent of the 1918 Spanish flu or the 2003 SARS pandemic - THESE viruses are airborne and can thus rapidly infect large groups of people Infection is transmitted from Infected(I) individuals via air/contact to Susceptible(S) individuals. Infected individuals recover and develop immunity or die, and are removed from the infection process (R)

(56) References Cited

U.S. PATENT DOCUMENTS

| | | | |
|---|---|---|---|
| 8,453,044 B2* | 5/2013 | Markus et al. | 715/205 |
| 8,577,886 B2* | 11/2013 | Markus et al. | 707/738 |
| 8,595,161 B2* | 11/2013 | Bearman et al. | 706/17 |
| 8,635,217 B2* | 1/2014 | Markus et al. | 707/734 |
| 8,880,521 B2* | 11/2014 | Markus et al. | 707/734 |
| 8,918,162 B2* | 12/2014 | Prokoski | 600/475 |
| 8,924,319 B1* | 12/2014 | Bearman | 706/17 |
| 2010/0097209 A1 | 4/2010 | Wong | |
| 2011/0093249 A1 | 4/2011 | Holmes et al. | |

OTHER PUBLICATIONS

Automated status identification of microscopic images obtained from malaria thin blood smears using bayes decision: A study case in plasmodium falciparum Anggraini, D. ; Nugroho, A.S. ; Pratama, C. ; Rozi, I.E. ; Pragesjvara, V. ; Gunawan, M. Advanced Comp Sci and Information System (ICACSIS), 2011 Intl Conf. on pp. 347-352.*

Accurate and efficient separation of left and right lungs from 3D CT scans: A generic hysteresis approach Ziyue Xu ; Bagci, U. ; Jonsson, C. ; Jain, S. ; Mollura, D.J. Engineering in Medicine and Biology Society (EMBC), 2014 36th Annual International Conf of the IEEE DOI: 10.1109/EMBC.2014.6945005 Publication Year: 2014 , pp. 6036-6039.*

Constructing Distributed Hippocratic Video Databases for Privacy-Preserving Online Patient Training and Counseling Jinye Peng ; Babaguchi, N. ; Hangzai Luo ; Yuli Gao ; Jianping Fan Information Technology in Biomedicine, IEEE Transactions on vol. 14 , Issue: 4 DOI: 10.1109/TITB.2009.2029695 Publication Year: 2010 , pp. 1014-1026.*

\* cited by examiner

Modeling basic viral dynamics requires a "viral strategy"

The main public health danger is a rapidly spreading, highly pathogenic airborne (respiratory) infection reminiscent of the 1918 Spanish flu or the 2003 SARS pandemic - THESE viruses are airborne and can thus rapidly infect large groups of people

S (110) → I (120) → R (130)

Infection is transmitted from Infected(I) individuals via air/contact to Susceptible(S) individuals. Infected individuals recover and develop immunity or die, and are removed from the infection process (R)

Fig. 1

How our system works: collect and analyze population-level information

Mobile device "raw" information may be used to create a highly realistic disease transmission model

210 — General coarse movement information (mobile device tracking services etc.)

→ 221 Locations of interest visited (e.g., clinic/hospital)
222 Movement pattern
223 Device usage pattern → 230 Create a "profile" for each user monitored (no private information). Define "normal"/baseline activity, indicative of a healthy state → 240 Compile information from multiple users in a geographic area

Fig. 2

| Defining local characteristic per infection, e.g. length of symptoms persistence per causing agent, range of symptoms, impact on wellbeing etc. 1010 |

| Defining location specific characteristics of a particular causing agent. 1012 |

| Combining user symptoms with local clinical data along with user location history to determine individual most probable causing agent responsible for the symptoms. 1014 |

| Identifying unique disease conditions by the identification of statistical variations (e.g., only one user has fever in an tire city, accompanied with knee pains bacterial infection emergency trip to the hospital). 1016 |

| Creating an ad-hoc "natural vaccination book" for each user, indicating potential infections user is resistant to or must be careful of. 1018 |

| Predicting region to region (e.g., city-to-city) transmission probability. 1020 |

| Enabling smart emerging disease detection systems. 1022 |

| Enabling smart environmental hazard detection systems. 1024 |

| Enabling smart disease containment strategies. 1026 |

| Enabling 'prevention measure success' quantification and analysis by time, or weather, or area, or population demography or any other system parameter relevant to disease propagation. 1028 |

| Predicting causing agent based on population wide symptoms, transmission characteristics, disease spread dynamics etc. 1030 |

| Creating general and specific disease warnings for users and health organizations, with or without prevention advice. 1032 |

Defining the local causing agent content at time t based on medical reports and available public and/or private clinical data( e.g ,.HMO internal reports ,hospital reports ,CDC public info etc 1102 ).

Correlating clinical symptoms with causing agent content at given time, by demographics (e.g., causing agent X causes symptoms Y in social group Z) 1104

Defining local symptom distribution in the area represented by the medical reports using a designated application( referred to here as" VirusTracker ,"VT ,)reports from HMOs ,or any other means of reporting which are accessible 1106

Creating a retrospective and real-time analysis of outcomes by following users symptoms over time until disease state is resolved 1108

Creating a retrospective and real-time definition of 'warning signals' indicating a disease requires further attention based on hospital/treatment history 1110

Clustering sets of symptoms by demographics and/or location and/or nature of symptoms and/ or retrospective analysis of outcome (as defined above) 1112

When available, matching individuals' location and location history with causing agent to create a past and current mapping of location of causing agents in given areas 1114

Creating potential 'transmission pathways' based on users' location, population density and causing agents in a given area 1116

Defining the 'density' of causing agent in the population from above 1118

Correlating causing agent with particular sets of symptoms – note these sets of symptoms vary between demographic and other groups (such as infection history of individuals comprising the groups) and also vary with time/environmental conditions. E.g., symptoms of influenza infection in a given area in March may vary from symptoms of the same infection in December (based on weather, sequence variation, host status etc.) 1120

For each diagnosis case, calculating the probability of a particular causing agent based on user past location, past infections (of user), symptoms and the various causing agent density in the areas visited by user on relevant time-scale (i.e., time that would match symptoms appearing at time t) 1122

For each user - calculating the most probable "symptom course" (i.e., disease manifestation over time) based on population-wide symptoms for most probable causing agents and individual history of user, along with user-reported various details such as stress-level, exercise, hours of sleep etc. 1124

Conveying to a user (or authorized health organization) the most probable causing agent and/ or the likely disease course (in terms of symptoms) based on the above 1126

Detecting statistical anomalies in user symptoms requiring further medical attention and issue specific warnings to user and to caretaker/physician defining the nature of the anomaly 1128

Continuously updating disease course definition and statistical range as well as update causing agent density based on the addition of clinical data and/or users symptoms. 1130

Determining, by the computerized system, that a first person is infected by a first infectious disease; wherein the determination is associated with a first person infection probability attribute. 1210

Detecting, by the computerized system, based upon location information collected during at least a portion of a first infectious disease manifestation period and indicative of locations of the first persons and other persons, a second person that was within an infection distance from the first person and is potentially infected by the first infectious disease. 1220

Calculating, by the computerized system, a second person infection probability attribute. 1230

Updating, by the computerized system, the first person infection probability attribute in response to the second person infection probability attribute. 1240

Receiving, by a computerized system, (a) location information relating to locations of multiple persons within a certain period of time; (b) clinical symptoms information related to one or more out of (a) at least one person of the multiple persons or (b) at least one of the locations. 1310

Evaluating, by the computerized system, probabilities of infections of the multiple persons by at least one infectious disease, in response to the location information and to the clinical symptoms information. 1320

Creating a table of patients containing demographics, reason for hospitalization, location in hospital, treatments received, treatment/analysis rooms visited and relevant clinical test results. 1710

Processing location data to create a list of locations visited including 'time stamps' containing time entered into location and time leaving the location. 1720

Calculating the epidemiological distances at any given time between two users. The epidemiological distance may be responsive to contact coefficients of different locations representing the likelihood of transmission in the area. 1730

Creating a network of patients based on the pair-wise distances between patents. 1740

Adding clinical data information to the network to establish potential disease paths. 1750

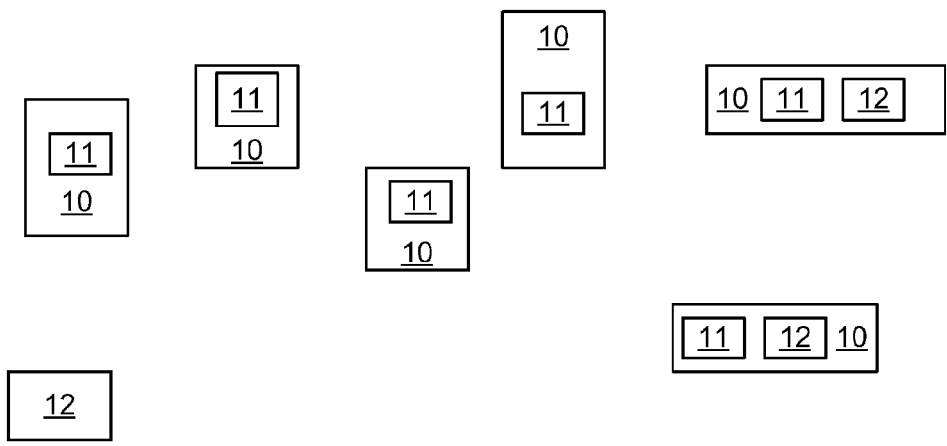
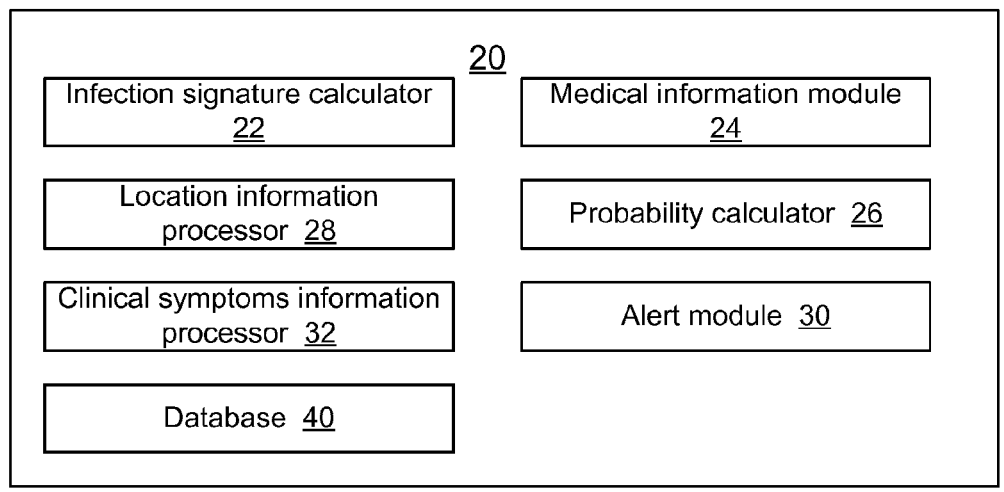
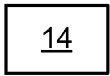
Fig. 19

SYSTEM AND METHOD TO ENABLE DETECTION OF VIRAL INFECTION BY USERS OF ELECTRONIC COMMUNICATION DEVICES

RELATED APPLICATIONS

This application claims the priority of U.S. provisional patent Ser. No. 61/561,884 filing date Nov. 20, 2012, which is incorporated herein by reference.

FIELD OF THE INVENTION

The invention relates generally to viral infection, and, more particularly, to a system and method to enable detection of viral infection by users of electronic communication devices.

BACKGROUND OF THE INVENTION

An infection is the colonization of a host organism by parasite species. Infecting parasites seek to use the host's resources to reproduce, often resulting in disease. Colloquially, infections are usually considered to be caused by microscopic organisms or microparasites like viruses, prions, bacteria, and viroids, though larger organisms like macroparasites and fungi can also infect.

Hosts normally fight infections themselves via their immune system. Mammalian hosts react to infections with an innate response, often involving inflammation, followed by an adaptive response. Pharmaceuticals can also help fight infections.

In order for infecting organisms to survive and repeat the cycle of infection in other hosts, they (or their progeny) must leave an existing reservoir and cause infection elsewhere. Transmission of infections can take place via many potential routes. Infectious organisms may be transmitted either by direct or indirect contact. Direct contact occurs when an individual comes into contact with the reservoir. This may mean touching infected bodily fluids or drinking contaminated water or being bitten by the deer tick. Direct contact infections can also result from inhalation of infectious organisms found in aerosol particles emitted by sneezing or coughing. Another common means of direct contact transmission involves sexual activity—oral, vaginal, or anal sex.

Indirect contact occurs when the organism is able to withstand the harsh environment outside the host for long periods of time and still remain infective when specific opportunity arises. Inanimate objects that are frequently contaminated include toys, furniture, door knobs, tissue wipes or personal care products from an infected individual. Consuming food products and fluid which have been contaminated by contact with an infecting organism is another case of disease transmission by indirect contact.

The main public health danger is a rapidly spreading, highly pathogenic airborne (respiratory) infection reminiscent of the 1918 Spanish flu or the 2003 SARS pandemic. These viruses are airborne and can thus rapidly infect large groups of people.

SUMMARY OF THE INVENTION

According to an embodiment of the invention a method may be provided and may include performing any of the stages illustrated in the specification and/or drawings.

Further embodiments of the invention include a computer readable medium that is non-transitory and may store instructions for performing the above-described methods and any steps thereof, including any combinations of same. For example, the computer readable medium may store instructions for executing, by a computerized system, any of the stages illustrated in the specification and/or drawings. Any reference to a method should be interpreted as including a reference to a non-transitory computer readable medium that stores instructions for executing the method by a computerized system. Any reference to a non-transitory computer readable medium should be interpreted as referring to a method that is executing according to the instructions stored at the non-transitory computer readable medium.

The computerized system includes at least one hardware component.

Additional embodiments of the invention include a computerized system arranged to execute any or all of the methods described above, including any stages—and any combinations of same.

There may be provided, according to an embodiment of the invention, a non-transitory computer readable medium that may store instructions for causing a computerized system to perform the following operations: determining, by the computerized system, that a first person is infected by a first infectious disease; wherein the determination is associated with a first person infection probability attribute; detecting, by the computerized system, based upon location information collected during at least a portion of a first infectious disease manifestation period, the location information being indicative of locations of the first person and other persons, a second person that was within an infection distance from the first person and is potentially infected by the first infectious disease; calculating, by the computerized system, a second person infection probability attribute; and updating, by the computerized system, the first person infection probability attribute in response to the second person infection probability attribute.

The determining may be responsive to at least one of (a) first person medical information fed by the first person, and (b) clinical information related to at least one of the first person and the first infectious disease.

The determining may be responsive to signatures of multiple infectious diseases.

The location information may be collected from hand held devices of the persons.

The location information may be collected from short-range transmission devices carried by the persons.

The location information may be collected from long-range transmission devices carried by the persons.

The determining and the calculating are responsive to demographic information relating to the first and second persons and to a demographic element of the signature of the first infectious disease.

The computer readable medium may store instructions for updating, by the computerized system, the first person infection probability attribute and the second person infection probability attribute in response to clinical symptoms information relating to at least one of the first person, second person and the first infectious disease.

There may be provided, according to an embodiment of the invention, a non-transitory computer readable medium that may store instructions for causing a computerized system to perform the following operations: receiving, by a computerized system, (a) location information relating to locations of multiple persons within a certain period of time; (b) clinical symptoms information related to one or more out of (a) at least one person of the multiple persons or (b) at least one of the locations; and evaluating, by the computerized system, probabilities of infections of the multiple persons by at least one infectious disease, in response to the location information and to the clinical symptoms information.

The non-transitory computer readable medium may store instructions for generating a person infection alert if a probability of infection of the person by an infectious disease exceeds a first threshold; and for transmitting the person infection alert to at least the person.

The non-transitory computer readable medium that may store instructions for generating a geographical zone infection alert if probabilities of at least a predefined number of persons that were, during the certain period of time, within the geographical infection alert exceed a second threshold; and for transmitting the geographical zone infection alert to a plurality of persons.

The non-transitory computer readable medium that may store instructions for calculating infectious disease signatures in response to the location information and to the clinical symptoms information.

The non-transitory computer readable medium that may store instructions for receiving by the computerized system, medical information provided by the persons; and wherein the evaluating, by the computerized system, of the probabilities of infections of the multiple persons may be further responsive to medical information provided by the persons.

The non-transitory computer readable medium that may store instructions for receiving by the computerized system, medical information sensed by mobile devices of the multiple persons; and wherein the evaluating, by the computerized system, of the probabilities of infections of the multiple persons may be further responsive to medical information provided by the persons.

The non-transitory computer readable medium that may store instructions for receiving voice information sensed by mobile devices of the multiple persons; and processing the voice information to detect disease related voices.

The non-transitory computer readable medium that may store instructions for calculating, by the computerized system, infections disease transmission pathways based upon the location information and the clinical symptoms information.

There may be provided, according to an embodiment of the invention, a non-transitory computer readable medium that may store instructions for causing a computerized system to perform the following operations: receiving, by a computerized system,
(a) location information relating to locations of multiple persons at different points of time; and (b) medical information that may include at least one of (i) medical information fed by at least one person; (ii) medical information sensed by at least one mobile device of at least one person; (iii) clinical symptoms information related to at least one person; and (iv) medical symptoms information related to at least one of the locations; and
calculating by the computerized system and in response to the location information and to the medical information, infectious diseases signatures that comprise spatial and temporal characteristics of a distribution of the infections diseases.

The non-transitory computer readable medium that may store instructions for evaluating, by the computerized system, probabilities of infections of the multiple persons by at least one infectious disease, in response to the location information and to the, infectious disease signatures.

The non-transitory computer readable medium that may store instructions for receiving by the computerized system demographic information related to at least one of the locations; and calculating by the computerized system and in response to the location information, the medical information and the demographic information, infectious diseases signatures that may include environmental condition, spatial and temporal characteristics of the distribution of the infections diseases.

The non-transitory computer readable medium that may store instructions for receiving by the computerized system environmental information related to the multiple locations persons; and calculating by the computerized system and in response to the location information, the medical information and the demographic information, infectious diseases signatures that comprise demographic, spatial and temporal characteristics of the distribution of the infections diseases.

There may be provided, according to an embodiment of the invention, a non-transitory computer readable medium that may store instructions for causing a mobile device of a person to perform the following operations: obtaining person medical information, wherein the person medical information is obtained by at least one out of (i) receiving person medical information from the person and (iii) sensing person medical information; detecting person location information indicative of locations of the person during multiple points in time; sending the person location information and the person medical information to a computerized system; receiving from the computerized system a person infection alert that is generated in response to person location information gathered from multiple persons and in response to medical information; person medical information from at least one person; and informing the person that the person is suspected as being infected by the infectious disease.

There may be provided, according to an embodiment of the invention, a non-transitory computer readable medium that may store instructions for causing a computerized system to perform the following operations: receiving, by a computerized system, (a) location information relating to locations of multiple persons within a certain period of time; (b) medical information related to at least one person of the multiple persons or (b) at least one of the locations; and (c) environmental information relating to at least one of the locations; and evaluating, by the computerized system, probabilities of infections of the multiple persons by at least one infectious disease, in response to the location information, to the medical information and to the environmental information.

There may be provided, according to an embodiment of the invention, a method to be executed by a computerized system, the method may include: determining, by the computerized system, that a first person is infected by a first infectious disease; wherein the determination is associated with a first person infection probability attribute; detecting, by the computerized system, based upon location information collected during at least a portion of a first infectious disease manifestation period and indicative of locations of the first persons and other persons, a second person that was within an infection distance from the first person and is potentially infected by the first infectious disease; calculating, by the computerized system, a second person infection probability attribute; and updating, by the computerized system, the first person infection probability attribute in response to the second person infection probability attribute.

There may be provided, according to an embodiment of the invention, a method to be executed by a computerized system, the method may include: receiving, by a computerized system, (a) location information relating to locations of multiple persons within a certain period of time; (b) clinical symptoms information related to one or more out of (a) at least one person of the multiple persons or (b) at least one of the locations; and evaluating, by the computerized system, probabilities of infections of the multiple persons by at least one infectious disease, in response to the location information and to the clinical symptoms information.

There may be provided, according to an embodiment of the invention, a method to be executed by a computerized system, the method may include: receiving, by a computerized system, (a) location information relating to locations of multiple persons at different points of time; and (b) medical information that may include at least one of (i) medical information fed by at least one person; (ii) medical information sensed by at least one mobile device of at least one person; (iii) clinical symptoms information related to at least one person; and (iv) medical symptoms information related to at least one of the locations; and calculating by the computerized system and in response to the location information and to the medical information, infectious diseases signatures that comprise spatial and temporal characteristics of a distribution of the infections diseases.

There may be provided, according to an embodiment of the invention, a method to be executed by a mobile device of a user, the method may include: obtaining person medical information, wherein the person medical information is obtained by at least one out of (i) receiving person medical information from the person and (iii) sensing person medical information; detecting person location information indicative of locations of the person during multiple points in time; sending the person location information and the person medical information to a computerized system; receiving from the computerized system a person infection alert that is generated in response to person location information gathered from multiple persons and in response to medical information; person medical information from at least one person; and informing the person that the person is suspected as being infected by the infectious disease There may be provided, according to an embodiment of the invention, a method to be executed by a computerized system, the method may include receiving, by a computerized system, (a) location information relating to locations of multiple persons within a certain period of time; (b) medical information related to at least one person of the multiple persons or (b) at least one of the locations; and (c) environmental information relating to at least one of the locations; and evaluating, by the computerized system, probabilities of infections of the multiple persons by at least one infectious disease, in response to the location information, to the medical information and to the environmental information.

BRIEF DESCRIPTION OF THE DRAWINGS

In order to understand the invention and to see how it may be carried out in practice, a preferred embodiment will now be described, by way of a non-limiting example only, with reference to the accompanying drawings, in the drawings:

FIG. 1 is a schematic drawing of the "viral strategy," constructed according to the principles of the present invention;

FIG. 2 is a flow chart illustration of the collection and analysis of population-level information, constructed according to the principles of the present invention;

FIG. 10 illustrates a method according to an embodiment of the invention;

FIG. 11 illustrates a method according to an embodiment of the invention;

FIG. 12 illustrates a method according to an embodiment of the invention;

FIG. 13 illustrates a method according to an embodiment of the invention;

FIG. 17 illustrates a method according to an embodiment of the invention;

FIG. 19 illustrates a computerized system and its environment according to an embodiment of the invention.

DETAILED DESCRIPTION OF PREFERRED EMBODIMENTS

Figure 3:
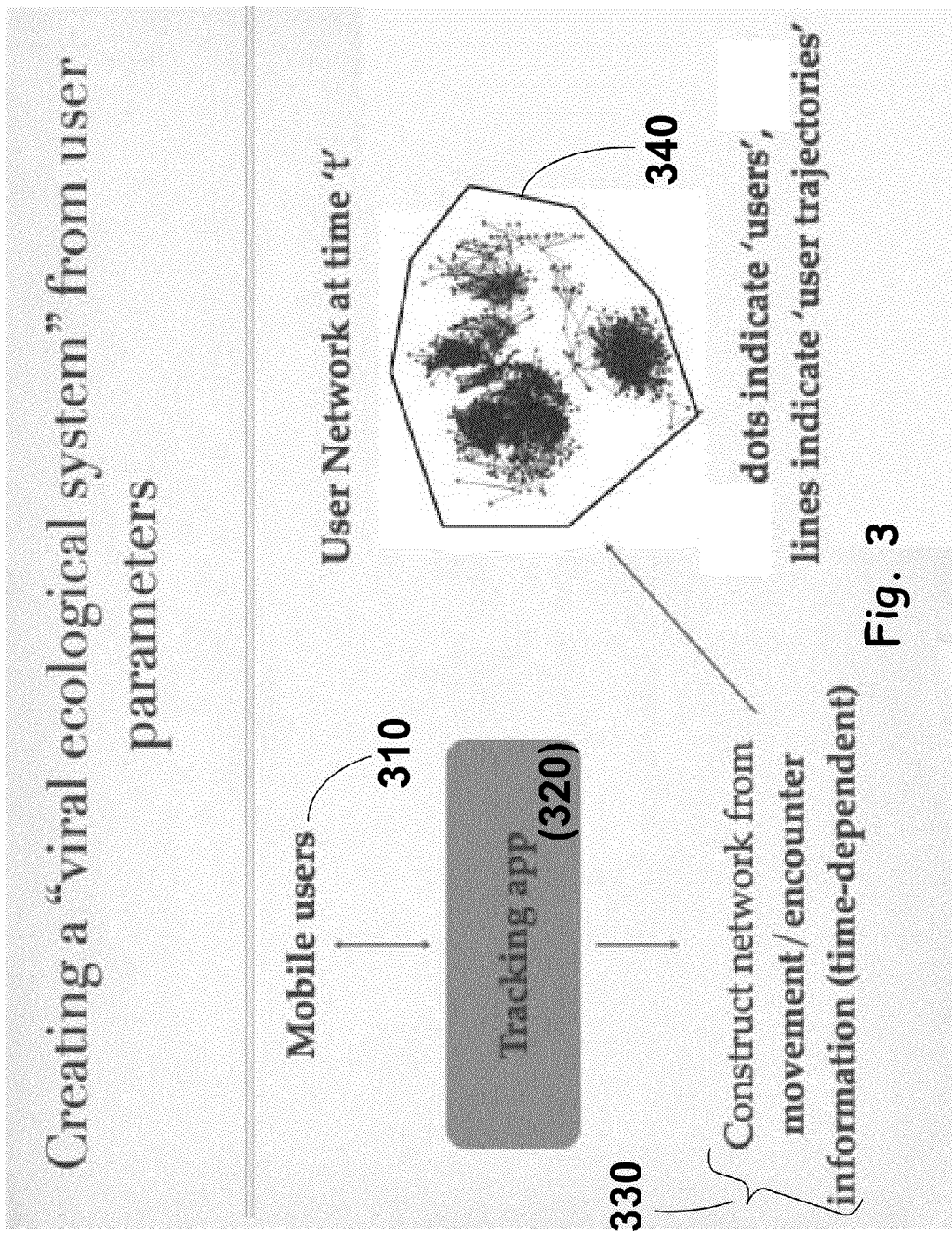
FIG. 3 is a schematic drawing of the creation of a "viral ecological system," constructed according to the principles of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that can be executed by the system and should be applied mutatis mutandis to a non-transitory computer readable medium that stores instructions that can be executed by the system.

Any reference in the specification to a non-transitory computer readable medium should be applied mutatis mutandis to a system capable of executing the instructions stored in the non-transitory computer readable medium and should be applied mutatis mutandis to method that can be executed by a computer that reads the instructions stored in the non-transitory computer readable medium.

The principles and operation of a method and an apparatus according to the present invention may be better understood with reference to the drawings and the accompanying description, it being understood that these drawings are given for illustrative purposes only and are not meant to be limiting.

Accordingly, it is a principle object of the present invention, based on meta-analysis of information gathered from the provider (e.g., AT&T), the device and the user of the application himself to provide an indication to a mobile device (e.g. smartphone) user of vicinities in which he may be at increased risk of contracting viral infections and also provide information regarding other quality of life regarding environmental phenomena (air pollution, noise, and due to the presence in that area of an increased number of viral disease carrying 'suspects' etc. due to the presence in that area of an increased number of viral disease carrying 'suspects') due to the presence in that area of an increased number of viral disease carrying 'suspects' due to the presence in that area of an increased number of viral disease carrying 'suspects'.

It is another principle object of the present invention, similarly based, to provide users with bio social feedback, using parameters gathered from the device it is possible to choose a profile from a list of predefined 'activity-profiles' (e.g., active, lazy, social, anxious etc.). The aim of the biosocial feedback is to help the user retain (or avoid) chosen activity-profiles for self-improvement and other purposes (support groups, challenge games on individual/group level etc.).

There are two primary methods utilized by the application in achieving the above aims:

Information about the General Population:

Indication of the activity level of the general population in that vicinity (e.g., all mobile users, all subscribers of a certain carrier, all users of a certain smartphone operating system). The level of activity can be derived from statistical attributes of the mobile devices present in that area. Statistical attributes can include motion as determined from the communication signals (GPS, cell tower, reception signal variance) and can be calibrated against the background of 'normal' behavior per a specific mobile device or per the "population" of mobile devices present in that specific area. This data requires cooperation from the providers. Also, the user must then "subscribe" to these sort of alerts.

General indications of the presence/absence of a large number of device-carrying individuals at specific types of establishments, e.g. a spike in the presence of individuals at local health centers (clinics) or absence from "normal" places such as "work place" or "gym" at specific periods. The workplace of an individual user may be inferred, for example by patterns of early travel to and late travel from the same location, Mondays through Fridays. Data may be correlated with seasons, weather, environmental data and national holidays.

Specific, local indications of the well-being or activity-profile of application users (or others that enable data collection). Well-being and/or activity-profile in general will be determined by the following parameters:

Any of the information available from the device's sensors (microphone, GPS, illumination sensor, vibration sensor, inclinometer, accelerometer, motion sensor, reception signal and camera) as well as any other sensors that may be added in the future to sample the users environment and provide information. In particular, information could be used to analyze the user's relative mobility or to identify specific indicators of viral symptoms (e.g. cough, changes in the user's voice). The information can be collected on a regular basis; following specific triggers (e.g. certain changes in behavior patterns, general indications of disease prevalence); or with active participation of the user (e.g. recording of cough, sensing of breathing etc.)

Data otherwise provided that can be linked to specific mobile devices such as on social networking sites or in other databases, which the application has access to, such as Google flu-trends.

Direct indications provided by users about their well-being. These could be self-initiated or in response to a prompt by the application (periodic, seasonal or due to suspicious patterns in the locality or related localities). Data may include subjective feeling of user, specific measurements preformed by device (e.g. breathing pattern), external measurements (e.g. body temperature) or expert opinion (e.g. diagnosis by a medical doctor) or indications of activity (e.g., met friends for dinner, missed a day at work for no reason, couldn't get up, etc.).

Specific information about the mobile device previous locations, such as healthcare facilities, which may correlate to a higher likelihood of infection.

The relevant 'vicinity' could refer to the immediate environment (e.g. office, restaurant), general geographic location (e.g. city) or users network environment (e.g. friends from users phonebook or user-defined friends or family) to provide an estimate of general disease and specifically lung/upper airways-related infections and other general environmental qualities (air quality, noise levels, etc.)

Another potential use of the application is to collect statistically significant data that would enable academic, disease control studies providing insights into the mechanisms of viral transmission and viral infection, both in general and for specific strains and even guide public-health measures.

The application may have various levels of privacy settings, controlling which information may be shared with others.

The application may be 'stand alone' or an added feature on another application (e.g., a mobile social networking application).

The application may be sold or distributed for free and may enable targeted advertising. Statistical information may be provided, with or without charge, to research institutions and commercial companies.

The application is not limited to viral/bacterial infections only. It may provide indications of other environmental phenomena (such as air quality) or used to identify other factors impacting individual well-being (e.g. asthma, heart condition). The camera associated with the user's smartphone could be used effectively to detect strap throat The application's primarily aim is to provide an indication to a mobile device (e.g. smartphone) user of vicinities in which he may be at increased risk of contacting viral infections due to the presence in that area of an increased number of viral disease carrying 'suspects.'

There are two primary methods for determining presence of such suspects:

Information about the General Population:

Indication of the activity level of the general population in that vicinity (e.g., all mobile users, all subscribers of a certain carrier, all users of a certain smartphone operating system) are noted. The level of activity can be derived from statistical attributes of the mobile devices present in that area. Statistical attribute can include motion as determined from the communication signals (GPS, cell tower, reception signal variance) and can be calibrated Vs. 'normal' behavior per a specific mobile device or per mobile devices present in that specific area.

General indications of the likelihood of presence of a large number of viral carrying suspects at a specific type of establishment (e.g. fitness center in specific periods) are noted.

Indication of the well-being of users of other device present in the same vicinity who are also users of the application or otherwise enable data collection which may indicate their well being. The well-being could be determined by:

Any of the information available from the device's sensors (microphone, GPS, illumination sensor, vibration sensor, inclinometer, accelerometer, motion sensor, reception signal and camera) as well as any other sensors that may be added in the future to sample the users environment and provide. In general information could be used to analyze the user's relative mobility or to identify specific indicators of viral symptoms (e.g. cough). The information can be collected on a regular basis; following specific triggers (e.g. certain changes in behavior patterns, general indications of disease prevalence); or with active participation of the user (e.g. recording of cough, sensing of breathing, etc, . . . ).

Data otherwise provided that can be linked to specific mobile devices such as on social networking sites or in other data bases which the application has access to.

Indications provided by users of their well being. These could be self initiated or in response to a prompt by the application (periodic or due to suspicious patterns)

Information about the mobile device previous locations, such as healthcare facilities may correlate to a higher likelihood of infection.

The relevant 'vicinity' could refer to use of the user's smartphone microphone, GPS and camera to sample the users environment, whether it is the immediate environment (e.g. office, restaurant, user himself), local environment (e.g. room), general geographic location (e.g. city) or users network environment (e.g. friends from users phonebook) to provide an estimate of general disease and specifically lung/upper airways-related infections and other general environmental qualities (air quality, noise levels, etc.)

Another aim of the application is to collect statistically significant data that would enable academic, drug-development, and disease control studies into the mechanisms of viral infection, both in general and for specific strains.

The application may have various levels of privacy setting controlling which information may be shared with others.

The application may be 'stand alone' or an added feature on another application (e.g. a mobile social networking application).

The application may be sold or distributed for free and may enable targeted advertising. Statistical information may be provided to with or without charge to research institutions and commercial companies.

The application is not limited to viral infections only. It may provide indications of other phenomena (such as air quality) or used to identify other factors impacting individual behavior (e.g. heart conditions).

The system and method may be adapted to:

Provide user with a basic indication of a potential viral infection of the user's lung, in accordance with FDA approval and liability issues;

Provide user with a basic indication of a potential viral infection of the user's upper airways/throat Provide user with a basic indication of a potential viral infection in the user's general geographic vicinity network-wise, that is, in connected friends like contact from users' phonebook Provide user with a basic indication of a potential viral infection in the user's general geographic vicinity geography-wise, that is, the amount of infections in a given geographic area (e.g., Palo Alto, Calif.)

Provide user with a basic indication of a potential viral infection in the user's specific geographic vicinity (e.g., the restaurant you have just entered), that is, in the area the user is present at Provide indication of air-quality in the users any geographic vicinity (e.g., smoke-filled area, level of micro-particles) and at various times during the day/week, where information is available (provided there are enough users of the application in the vicinity)

Provide indication of noise levels in any geographic vicinity (e.g., background noise levels, specific noises such as car horns) and at various times during the day/week, where information is available (provided there are enough users of the application in the vicinity)

Provide user with tools to perform a basic diagnosis of friends and relatives (e.g., children)—application will NOT replace an expert's evaluation, in accordance with any necessary FDA approvals.

Provide user with tools to perform a medical grade evaluation of self and relatives using specific hardware described below ("Smartoscope")

Provide health authorities with statistical data on symptom distribution in the population on a geographic basis Provide user with tools to follow his own current behavior pattern as defined by application and compare to his "normal self" pattern. App may then attempt to define "abnormal states" and help user correct if necessary. For example if depression is detected (e.g. through reduction in movement, changes in movement pattern, excessive sleep, subjective report of bad mood) the app may suggest immediate steps to take (kind of like a personal eTrainer . . . )

Indicate to user how his pattern differs from his normal self and if necessary guide user BACK into normal pattern in a sort of social/behavior-level bio social feedback Provide user with tools to follow his own current behavior pattern as defined by application and compare to the "Average population" pattern for fun or other purposes Allow user to define goals (e.g. "I want to be a bit more active") and provide feedback when goals are not met. This will be done using the parameters used by the app. For example the app may suggest going to visit the Gym again ("We have detected a drop at your exercise profile—are you feeling well? Could use a visit to the gym?" etc.)

"User states" may be defined using ALL parameters that may be monitored on the device such as specific tests designed for the application, the apps used, time spent using apps, user performance on these applications assuming they produce a result, time spent on phone, ratio of user talking to "other" (other person talking, silence) while on the phone, user velocity, user movement pattern etc. (?). The app may also ask or accept user specific input on parameters such as "Worked 2 extra hours every day", "spoke to my ex-girlfriend", "went to the gym" etc. Using GPS or specific info (use access to phonebook/SMS) the app may then allow user to keep track of these event without the user participation.

User state will be defined based on all or some of these parameters. User state is a dynamic application and may be either based on pre-defined profiles in the application ("social", "mobile", "active", "stressed", "focused" etc.) OR defined by the user as a combination of the pre-defined profiles (e.g., 30% active, 70% focused) or entirely by the user. After a state has been defined the app will update user on his progress in obtaining this state (i.e., biosocial feedback)

User may choose to SHARE states and add them to the app as "public user-defined states". User may add his name or nickname to these states (e.g., "The Galmogy state"). Only friends of user will see these states and may spread them (share) to their friends as well. Successful states (i.e., states that have been shared by over X users) may win prizes for user (crowd-sourcing)

User may CHALLENGE friends to "compete" in achieving these states (either user or pre-defined)

Users may form "groups" for any of the purposes above, wherein non-private group information will be shared with user for motivation, gaming or other purposes.

User may PUBLISH his results in his circle of friends or globally. Published results will never contain any private information unless specified so by user. That is, user may publish to his friends (contacts) or a subset of his friends that he is "100% focused" (i.e., achieving the goal of being 100% focused from the pre-defined states) or "60% stressed" but may also publish specific details such as "X has been 90% mobile this week, covering a distance of 230 km in 3 days"

User may publish results from aim 1-9 anonymously or not, in order to provide "health warnings" or "updates" to friends not using the application. Results will be published to specific contacts (from phonebook), all contacts or the general public of users. These publications may include warnings with various levels of specificity (e.g., "The application has detected a large spike in influenza like illness in Haifa/east palo-alto" etc.) or updates such as "X is no longer coughing and back to full capacity—mazal tov!"

User may "subscribe" to news from various areas, i.e., receive non-private updates from areas defined by user (e.g., if user subscribes to palo-alto for "disease related info" he will receive a summary of updates from users in that area). Only updates defined by the user as "public" will be shared with users outside of the user's contact list. Private information will never be shared publicly. With regard to all aspects of the application, private information such as actual sound bites recorded, specific measurements etc. will only be stored on the LOCAL device and discarded after relevant data has been extracted.

Methods:

The application (app) is based on data collected by service providers (AT&T etc.) and the intrinsic microphone, GPS, camera and all other accessible devices of the smartphone (phonebook, list of calls (incoming/outgoing/missed), SMS etc. and will operate on both the individual and the population level for comparison purposes (e.g., how much do I talk compared to the average). Private data will never be shared unless specified so by user.

Category 1: Creating Baseline Sick or Activity-Profiles

When first turned 'on', the app creates a baseline profile for each user defined by a set of parameters collected from the device. Each machine may contain profiles for multiple people as defined by user (e.g., me, my wife, my co-worker Jim etc.) Since only one person actually carries the device it is not possible to use some parameters, such as movement for all profiles. The parameters used to create the baseline profile include data collected from the device built-in modules (Microphone, camera, GPS, etc.) as well as from specifically designed or general external modules (thermometer, barometer, hygrometer or stato scope-like microphones for handheld devices (smartoscope described in Appendix 1)). This baseline profile will be updated regularly with user consent and will require the user to be in a "normal" state when it is created. Over time the application can create an "average" baseline and define the standard deviation for each parameter recorded and for the parameter set as a whole. All the data collected will be stored by default only locally on the device itself to prevent privacy issues.

Similarly, the user will be encouraged to notify the app when "feeling sick" (or other situations such as: vacation, anxious, social, work etc.) to allow the app to create a defined parameter activity-profile for these "states". It may also become more specific and divide "states" into levels, e.g. "sick" into light vs. severe, stomach vs. airways etc., "anxious" into light stress, heavy stress or even types of stress (work, social etc.)

For the user activity-profiles it creates the application will monitor sound (built-in microphone), movement (GPS/cell tower, inclinometer, vibrations), picture and illumination (Built-in camera). Sound monitoring includes parameters such as speech, background noise, heart-rate, sound of air going through the upper/lower airways, cough, sneeze, pitch of voice when talking time spent on phone, using applications etc. Movement monitoring includes total distance traveled (per hour or part of it, per day), speed, and movement pattern of the user, vibrations, angle at which device is held when active etc. The camera can be used to monitor the eye and throat (color of tonsils, white dots on throat indicative of bacterial infection) as well as general appearance (fallen/sunken face etc.). Information from external devices may be fed in manually—body temperature, blood pressure, heart rate, subjective feeling, number of hours and quality of sleep etc.

Application Monitoring Modes

After creating these statistical baseline activity-profiles, the app will allow users to choose a surveillance level between active testing and full sentinel modes. In active testing mode (highest privacy setting) the app will NOT run in the background and will only "monitor" when the user activates it for a particular purpose—for example to define a "disease state", check the color of the user's throat (not easy by eye), measure any of the other parameters or even for checking how "normal" his/her behavior has been on that day/week, compared to the "normal" baseline.

In full sentinel mode (most "socially-aware" mode) the app will run in the background and periodically "sample" or "monitor" the user and the environment for the parameters used in the user's profile. The level of monitoring is determined by privacy settings, so there are a few possible modes, not just "0 and 1."

Thus in this mode the app can refine over time its definitions for what is a "Normal profile" and how the "normal environment" sounds like. When the normal profile changes significantly enough (e.g. outside 2 STD) the app will alert user that is has detected a potential "change-of-state" and prompt user to indicate what is the cause of this change in observed pattern, e.g. if a disease-like activity-profile has been detected it will prompt: "We have noticed a significant change in your behavior pattern and cough—are you feeling well?" If the answer is that the user is feeling well it will adjust the normal profile and/or try to find a different state that matches the particular activity-profile detected. If the user indeed does not feel well it will prompt further actions such as measuring temperature, taking pictures of throat, using microphone as a statoscope (see Appendix 1 below) etc. In the case of the application used as a semi-diagnostic tool, at the end of the analysis process it will offer the user its non-medical opinion and ask for user feedback to improve the analysis. Feedback will be either from user subjective feeling (symptoms have passed after 2 days and I'm feeling better) or from medical expert (I was diagnosed with flu-like illness). If user was indeed feeling sick or diagnosed as sick by the professional it will define the pattern observed as a "strong disease state". If this disease state is detected again it will suggest going to clinic for further expert diagnosis by a prompt saying: "last time you displayed this pattern it was diagnosed by the physician as a case of the Flu—it is likely your symptoms indicate a flu-like illness". The same holds for other states defined by the other activity-profiles.

In both active and sentinel modes and with user permission, private data will be stored locally on the device while non-private summary of data will be sent to a secure database where all consenting users non-private profile will be used for scientific pandemic evaluations on the population level, defining population-level activity-profiles (i.e., an average "anxious state" profile etc.) and research. Users will have varying levels of privacy settings to choose from.

The most extreme privacy setting would allow no transmission of information about the user at all, i.e. only reception of alerts for user vicinity, but the system and method may most likely limit the data provided to such users. The user will also have an option to allow his data to be used for improvements to the application and scientific research.

NOTE that statistical data from all users may be used to improve the definition of "states" on the individual level; e.g., data from the user's environment such as number of identified disease cases in the same geographic region will be used as a "population-level" parameter used for epidemic-potential evaluation, i.e., using both user data as described above and adding to that the prevalence of disease in geographic and network vicinity in providing an opinion/feedback.

Application Environmental Warnings and Population-Level Data

Data contributed by ALL users that are willing to share non-private information will be used to define "normal" vs. "abnormal" environments (i.e., high proportion of infections, noise, pollution, active people etc.). For example, if many users in a particular location (e.g. a city) display individual signs of flu-like illness at a given time-point then the system will mark that city accordingly and notify users that the area displays high frequency of disease cases.

Similarly, when going to an event (music festival) user can check in advance whether the area displays signs of high concentration of sick people, if it has high levels of noise (currently or historically, see Appendix 2), are the users in the area displaying a "social" activity-profile etc. The system uses two independent methods to define these local conditions: the amount of users in the area displaying a particular activity profile (e.g., "sick") AND data contributed by "sentinel users" that provides insights into noise levels and other parameters monitored. Note that sentinel users will have the option to allow the app to monitor the environment by sound.

It is clear that a phone listening-in on an emergency room during the winter will contain a lot of wheezing, sneezing and coughing sounds. Thus it will be marked as "unhealthy." The app will also treat "network friends" as an environment.

Air-quality may be monitored in a similar fashion; the app may be used to monitor air quality in specific areas far more accurately (higher resolution) in a similar fashion to the one described above, by aggregating the amount of non-sick cough in specific areas. For example, if a substance that causes cough and sneezing (pollen, smoke) is abundant in a small geographic area (using GPS/phone location) then the app will detect a lot of non-sick coughing/sneezing and mark the area as "potential bad air quality area."

In an optional embodiment the microphone is used to diagnose airways:

Using the built-in microphone or a special "Smartoscope" (a microphone designed to mimic a stato scope) users may be able to diagnose with greater accuracy the condition of airways for themselves or family members such as infants. The app will prompt user to start test and graphically show user what actions to take, e.g. hold microphone at shown angle against this area for this time, breath in, breath out, cough etc.

The application (app) is based on the intrinsic microphone, GPS and camera of the smartphone and has two modes:
  Self-diagnosis
  Environmental (neighborhood) warnings.

All the above and other characteristics and advantages of the invention will be further understood through the following illustrative and non-limitative description of preferred embodiments thereof.

FIG. 1 is a schematic drawing of the "viral strategy," constructed according to the principles of the present invention. Modeling basic viral dynamics requires a "viral strategy." The main public health danger is a rapidly spreading, highly pathogenic airborne (respiratory) infection reminiscent of the 1918 Spanish flu or the 2003 SARS pandemic. These viruses are airborne and can thus rapidly infect large groups of people. Infection is transmitted from Infected (I) individuals 120 via air/contact to Susceptible(S) 110 individuals. Infected individuals recover and develop immunity or die, and are Removed from the infection process (R) 130.

FIG. 2 is a flow chart illustration of the collection and analysis of population-level information, constructed according to the principles of the present invention. The system works by collecting and analyzing population-level information Mobile device "raw" information may be used to create a highly realistic disease transmission model. General coarse movement information (mobile device tracking services, etc. 210.

Locations of interest visited (e.g., hospitals, clinics 221
  Movement pattern 222
  Device usage pattern 223
  Create a "profile" for each user monitored (no private information). Define "normal"/baseline activity, indicative of a healthy state 230. Compile information from multiple users in a geographic area 240.

FIG. 3 is a schematic drawing of the creation of a "viral ecological system" from user parameters, constructed according to the principles of the present invention. A tracking application 320 is applied to mobile users 310. A network is constructed from (time-dependent movement/encounter information 330. A user network at time 't' 340 is illustrated. The dots 341 indicate 'users,' the lines 342 indicate 'user trajectories.

Figure 4:
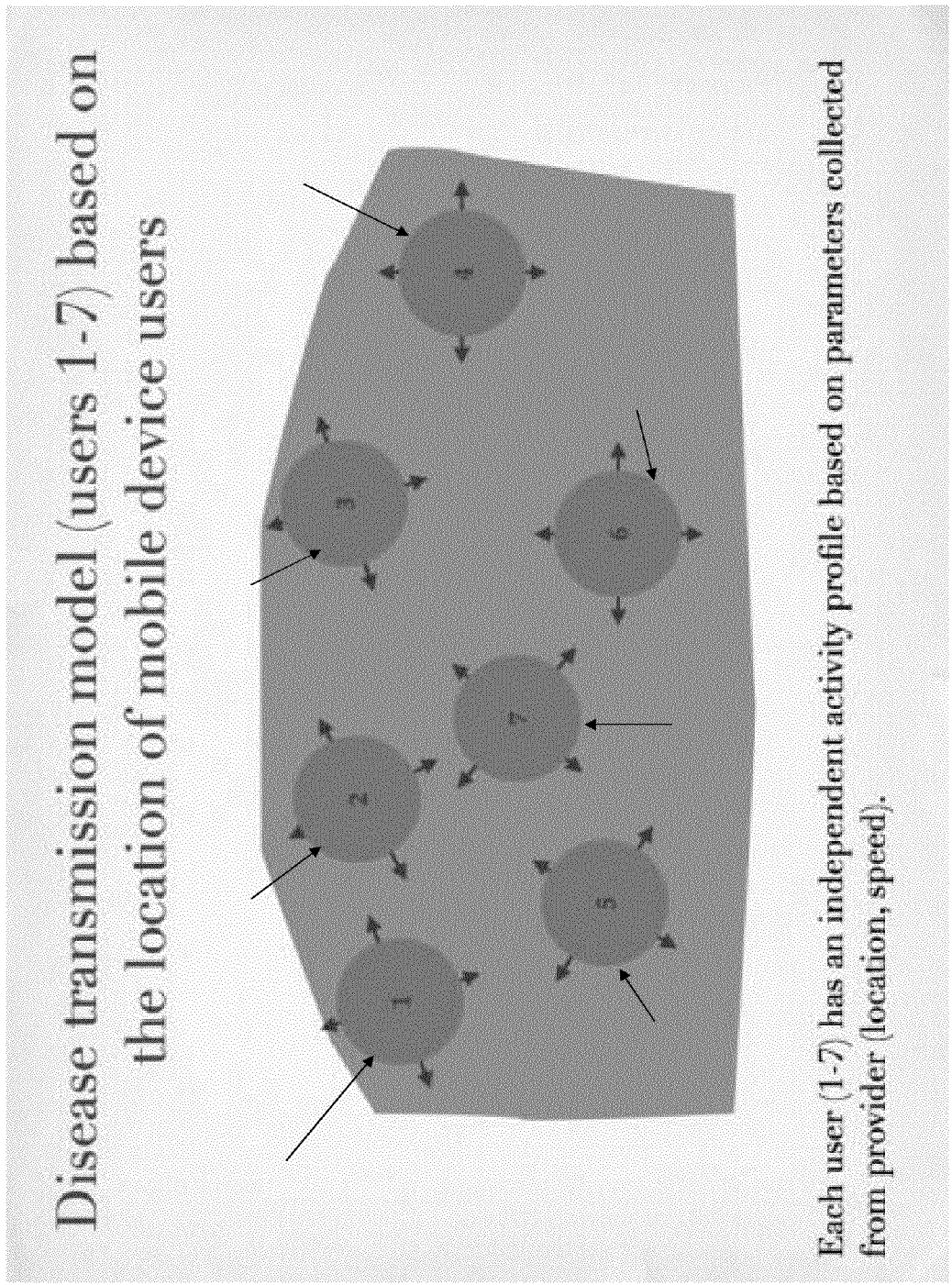
FIG. 4 is a schematic drawing of the disease transmission model, constructed according to the principles of the present invention.

FIG. 4 is a schematic drawing of the disease transmission model, constructed according to the principles of the present invention. Each user (410-470) has an independently profile based on parameters collected from provider (location, speed).

Figure 5:
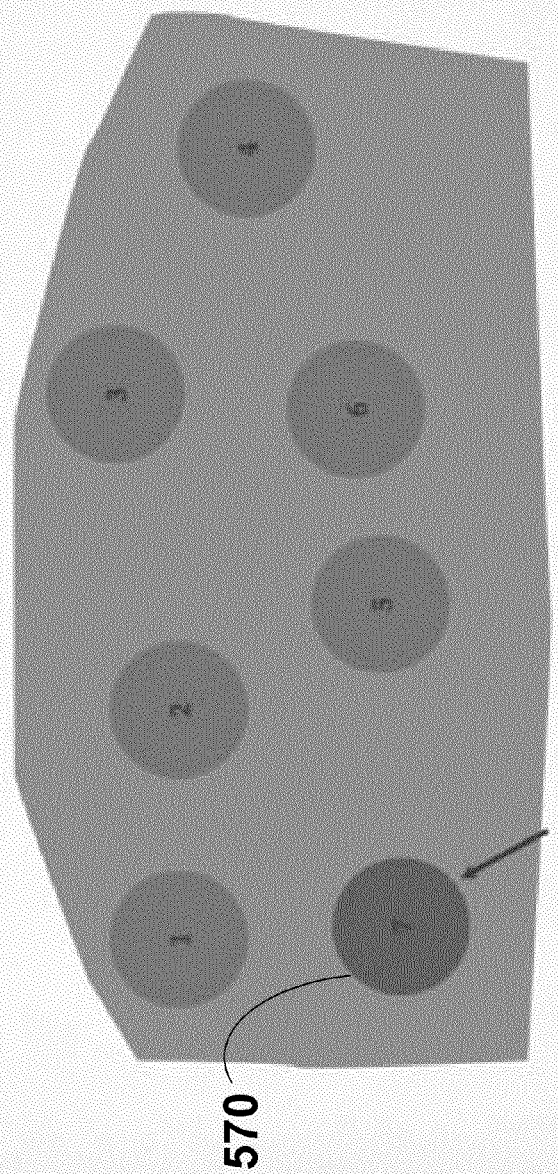
FIG. 5 is a schematic drawing of a seeded infection simulation, constructed according to the principles of the present invention.

FIG. 5 is a schematic drawing of a seeded infection simulation, constructed according to the principles of the present invention. A seed (or seeds) is chosen for an infection and the simulation is allowed to progress. 'User 7' 570 is arbitrarily designated as "infected." For simulation purposes one or several users are designated as "infected" The amount of time a user remains infected and the method of infection (e.g., time-spent together in a single location with other users) are disease-specific and constitute part of the "viral strategy."

Figure 6:
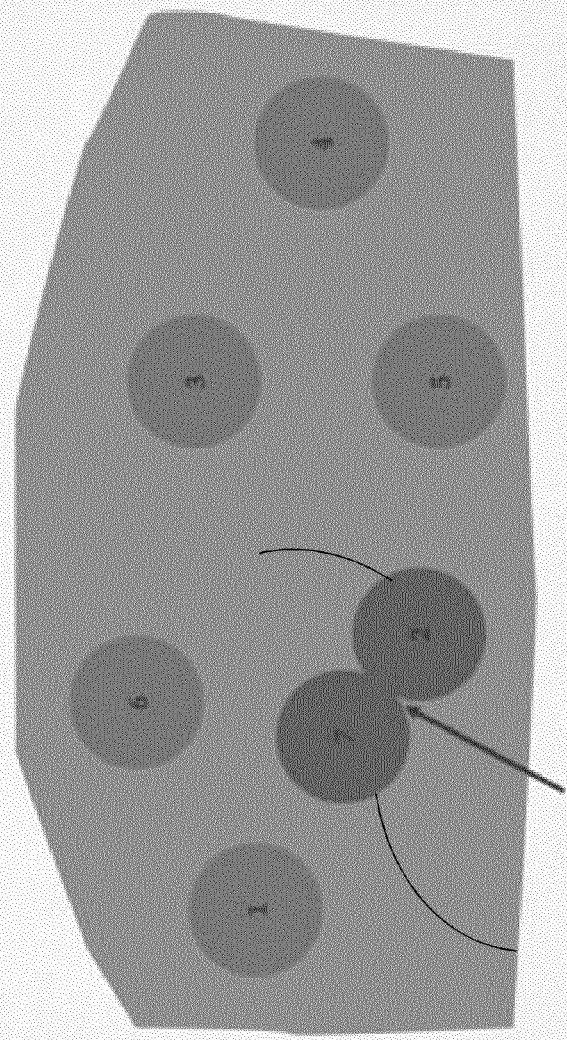
FIG. 6 is a schematic drawing of a "productive interaction," leading to a an infection event, constructed according to the principles of the present invention.

FIG. 6 is a schematic drawing of a "productive interaction," leading to an infection event, constructed according to the principles of the present invention. Interaction is depicted between an infected individual 670 and a susceptible individual 620. Using the general data available (location, time spent at various locations) the chain of resulting infections is determined, where each encounter has a probability p of effective transmission of the disease.

Figure 7:
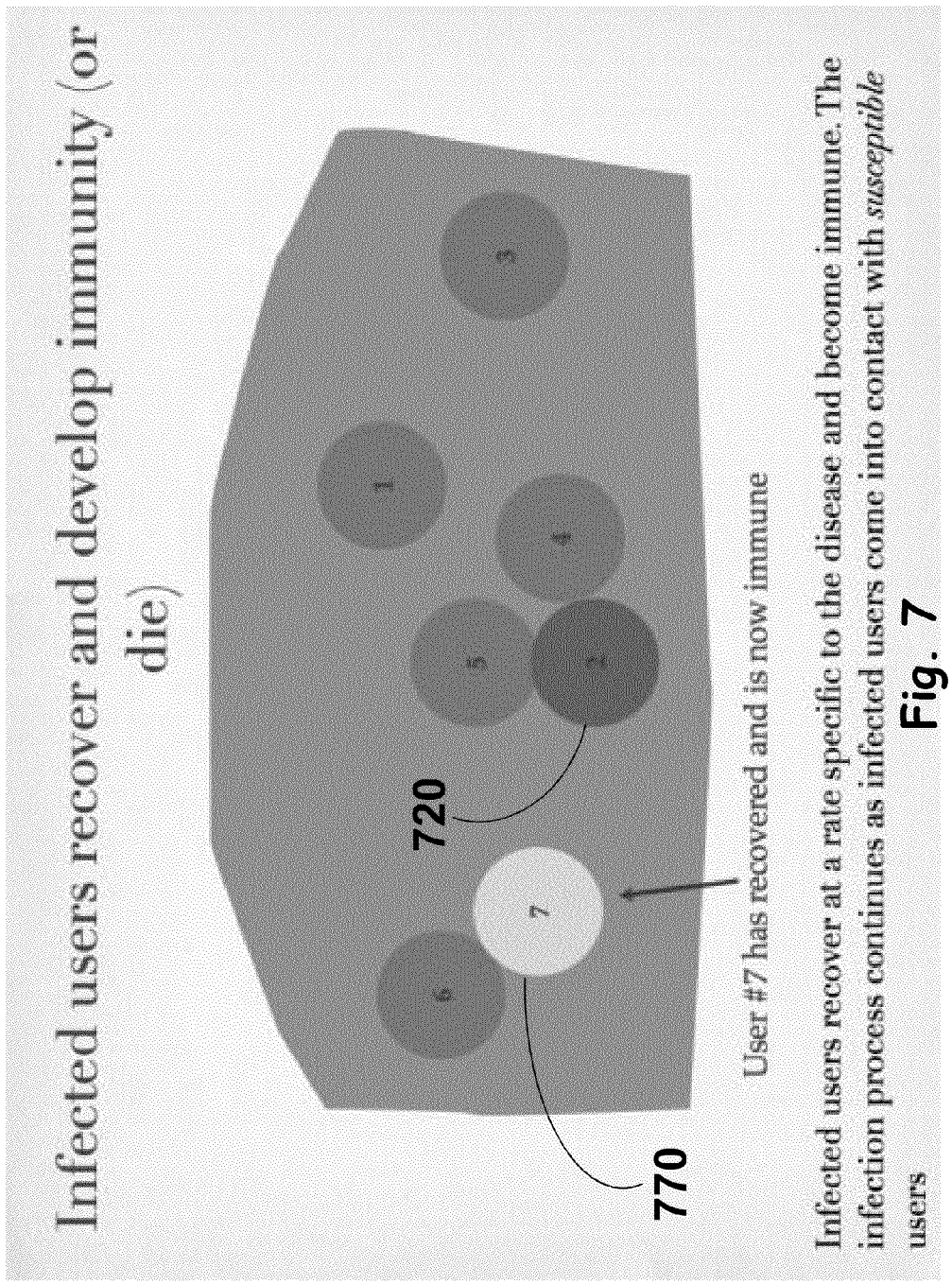
FIG. 7 is a schematic drawing of how infected users recover and develop immunity (or die), constructed according to the principles of the present invention.

FIG. 7 is a schematic drawing of how infected users recover and develop immunity (or die), constructed according to the principles of the present invention. Infected user 770 has recovered and is now immune, as symbolized by the white coloration. Infected users recover at a rate specific to the disease and become immune. The infection process continues as infected users come into contact with a susceptible user 720.

Figure 8:
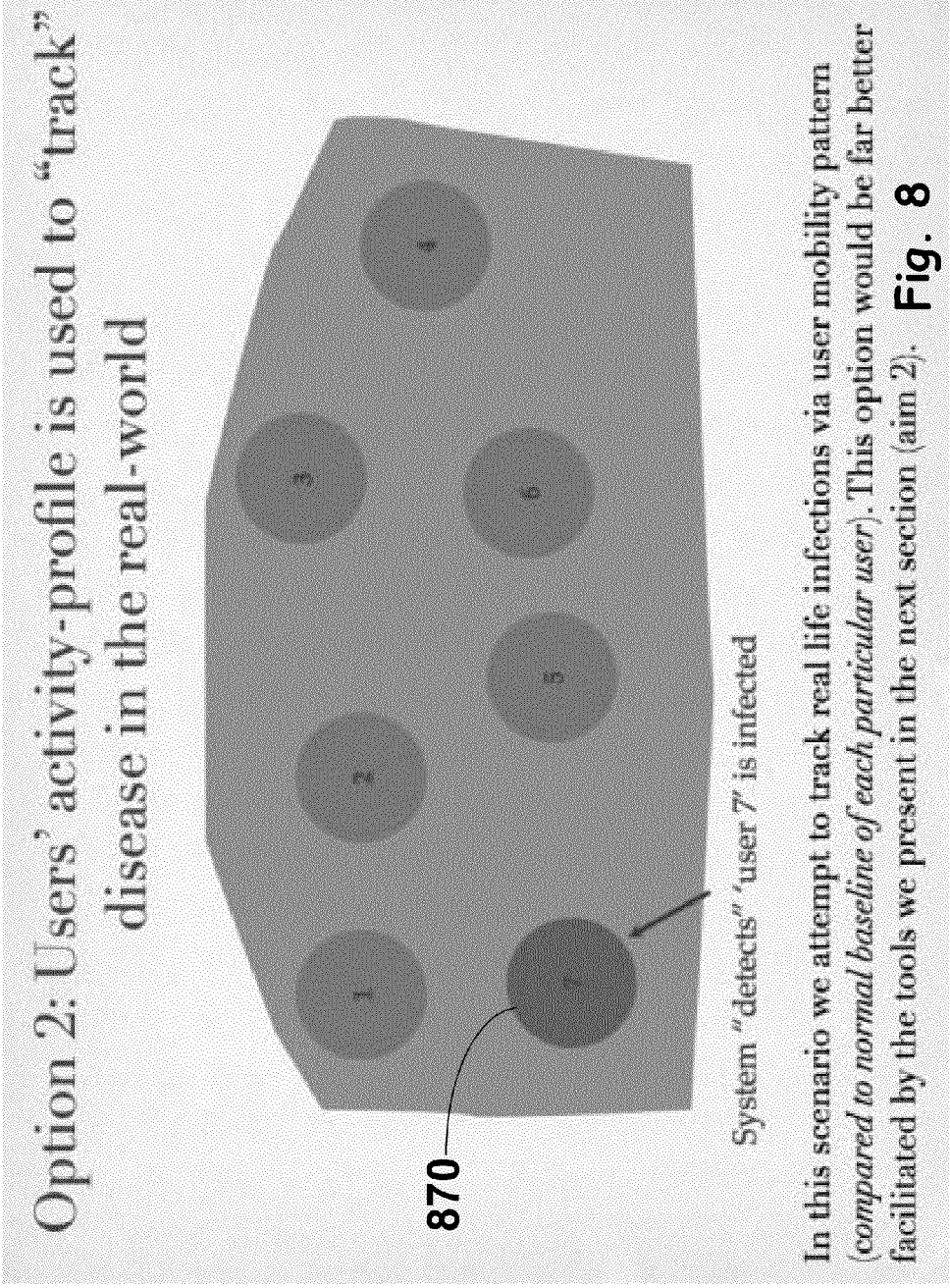
FIG. 8 is a schematic drawing of how an activity profile is used to "track" disease, constructed according to the principles of the present invention.

FIG. 8 is a schematic drawing of how a user activity profile is used to "track" disease, constructed according to the principles of the present invention. The system "detects" that 'user 870' is infected. In this scenario an attempt is made to track real life infections via user mobility patterns (compared to the normal baseline of each particular user). FIG. 8 represents an optional embodiment: Historical vs. current values.

When looking at a particular, well-defined geographic area (a public park, a neighborhood, an office building) it is often very informative to look at historical values of parameters measured. This data may be divided into daily/weekly averages, averages by particular day, time of day and even correlated to weather conditions. Using these historical parameters the application can define different activity-profiles for geographic areas on similar lines as defining activity-profiles for users, in accordance with privacy issues. That is, an area may be defined as "quiet," "loud," "low-air quality," "active," etc., according to the parameters provided by application users.

Figure 9:
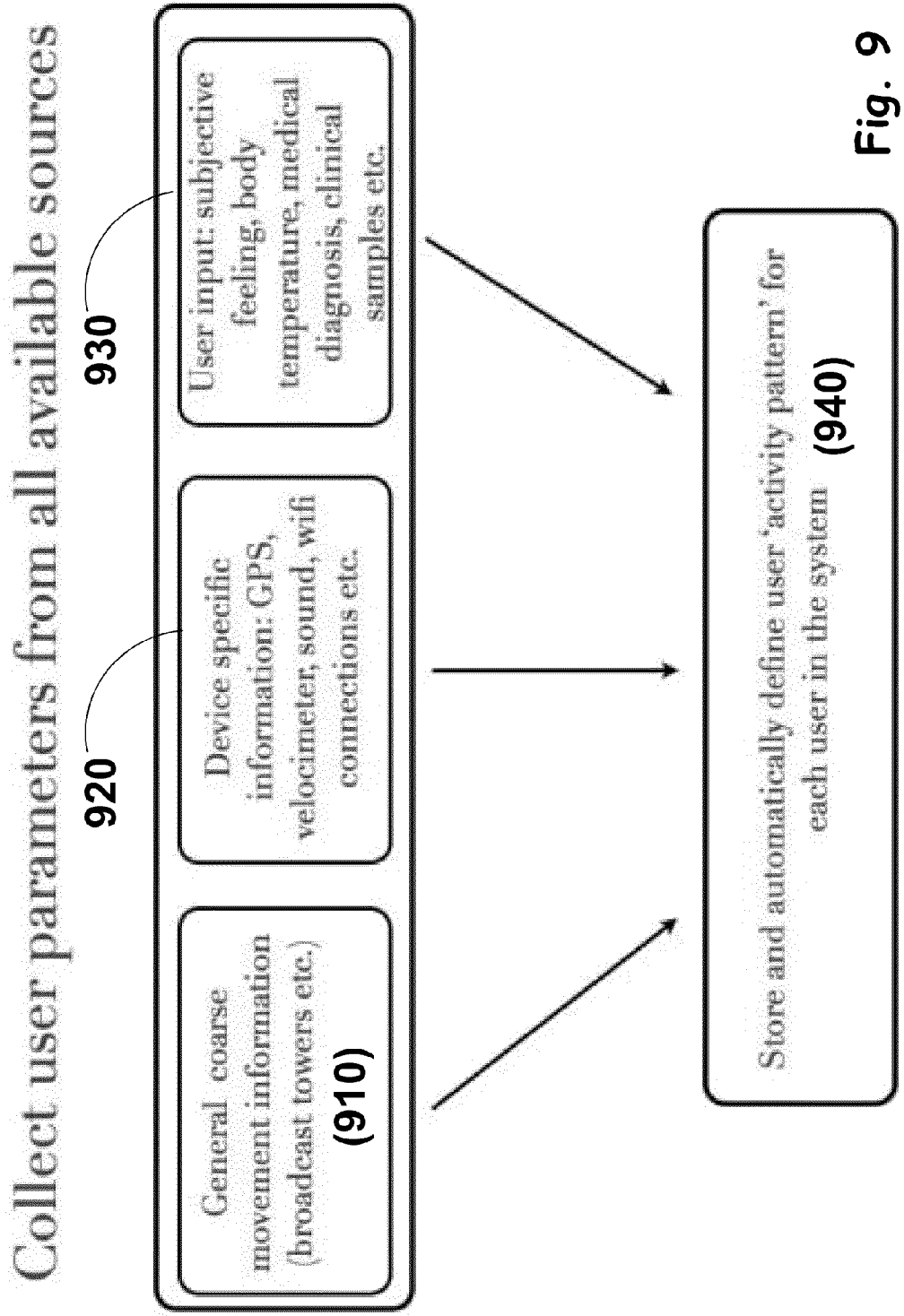
FIG. 9 is a flow chart illustration of the collection of user parameters, constructed according to the principles of the present invention.

FIG. 9 is a flow chart illustration of the collection of user parameters, constructed according to the principles of the present invention. General coarse movement information (broadcast towers, etc.) 910; device specific information: GPS, velocimeter, sound, wifi connections, etc. 920; user inputs: subjective feeling, body temperature, medical diagnosis, clinical samples, etc. 930 are stored, and automatically define user 'an activity pattern' for each user in the system 940.

The terms "user" and "person" are used in an interchangeable manner in this patent application.

According to various embodiments of the invention there is provided an automatic diagnostic system based on a combination of clinical diagnostic information (e.g., MOH publications, National surveys, Hospital data, MD personal reports etc.), environmental factors (weather, allergens, air-pollution), social connectivity structure and population-wide symptom reports (fever, cough, headache, sore throat, diarrhea etc. provided via dedicated smartphone application).

The system may use a transmission logic of infectious disease at the core of the decision-making process.

That is, infectious disease requires contact between individuals in order to be transmitted (whether be it direct or indirect contact via surface/air etc.). Moreover, most seasonal and non-seasonal infections appear in individual "peaks" (exact shape determined by local interaction profile and transmission route, see FIG. 1)—therefore the exact identification of few clinical samples per area at a given time have significant predictive power for the entire location at a particular time. This power is increased further when the movements and basic social connections of patients are added—as may be done using a location-tracking app and/or connections as they appear in social media (e.g. face book) or as reported by users. Our system is based on correlating the clinical samples diagnosed to user symptoms at a location in a given time, taking into considerations also the demographics, history and social environment of the user.

To provide the most exact results the system and method may use local clinical data, user reported symptoms and users location patterns to automatically create exact transmission chains and diagnosis based on "local disease content" (supplied by hospitals, HMOs, MDs, health organizations and labs), user location and local and/or global reported symptoms at a given time or over a longer period. As a result the system and method may be able to provide users with particular rather than 'general' diagnosis (i.e., the system and method may replace ILI (influenza-like-illness) with the exact causing agent of the ILI (e.g., RSV infection), the system and method may replace "stomach infections" with particular stomach infections (e.g. Salmonella.t) etc.), create detailed population-wide symptom database for particular disease strains and even provide users with accurate individual "infection history" showing users what they have been infected with (even when disease is sub-clinical) and automatically updated individuals' immunity tables' based on these past infections. Taken together patients will know exactly what they have been infected with, the course of the infection, how they responded to it, quantify how they responded to different treatment options (medication, nutrition, exercise, stress, life-style changes etc.), how it compares to the rest of the population and what immunity they have acquired.

Furthermore, given our knowledge of disease content in an area, its rate of spread and the demographics it affects the system and method may can provide users (and/or MDs/Hospitals/HMOs) with accurate individual disease warnings and the means to avoid them (vaccination/prophylactics/prevention).

There is provided a method (denoted 1000 in FIG. 10) that may include:

a. Defining (1010) local characteristic per infection, e.g. length of symptoms persistence per causing agent, range of symptoms, impact on wellbeing etc.

b. Defining (1012) location specific characteristics of a particular causing agent c. Combining (1014) user symptoms with local clinical data along with user location history to determine individual most probable causing agent responsible for the symptoms d. Identifying (1016) unique disease conditions by the identification of statistical variations (e.g., only one user has fever in an tire city, accompanied with knee pains→bacterial infection→emergency trip to the hospital)

e. Creating (1018) an ad-hoc "natural vaccination book" for each user, indicating potential infections user is resistant to or must be careful of f. Predicting (1020) region to region (e.g., city-to-city) transmission probability g. Enabling (1022) smart emerging disease detection systems h. Enabling (1024) smart environmental hazard detection systems i. Enabling (1026) smart disease containment strategies j. Enabling (1028) 'prevention measure success' quantification and analysis by time, or weather, or area, or population demography or any other system parameter relevant to disease propagation k. Predicting (1030) causing agent based on population wide symptoms, transmission characteristics, disease spread dynamics etc.

l. Creating (1032) general and specific disease warnings for users and health organizations, with or without prevention advice Infections travel via physical proximity and each causing agent has its own slightly unique properties of transmission. As a result the transmission of a particular causing agent (e.g., influenza, salmonella) in a population of a known structure may be predicted with great accuracy.

The system proposed combines for the first time location supplied by a smartphone application or by any other means (user report, HTML5 location, physical presence etc.) and the 'clinical content' in a defined geographic region, where clinical content may include of the laboratory analysis of clinical samples (RT-PCR results, DNA/RNA sequencing, growth on plates etc.), MD diagnostic reports (i.e., the supposed causing agent as diagnosed by an MD) and reported symptoms (either provided by user himself or medical/health facilities).

The diagnostic process the system and method may define here works in these stages described in more detail below; for each area and for each causing agent a method (denoted 1100 in FIG. 11) may be executed and may include:

a. Defining (1102) the local causing agent content at time t based on medical reports and available public and/or private clinical data (e.g., HMO internal reports, hospital reports, CDC public info etc.)

b. Correlating (1104) clinical symptoms with causing agent content at given time, by demographics (e.g., causing agent X causes symptoms Y in social group Z)

c. Defining (1106) local symptom distribution in the area represented by the medical reports using a designated application (referred to here as "VirusTracker", VT), reports from HMOs, or any other means of reporting which are accessible d. Creating (1108) a retrospective and real-time analysis of outcomes by following users symptoms over time until disease state is resolved e. Creating (1110) a retrospective and real-time definition of 'warning signals' indicating a disease requires further attention based on hospital/treatment history f. Clustering (1112) sets of symptoms by demographics and/or location and/or nature of symptoms and/or retrospective analysis of outcome (as defined above). This may include automatically clustering symptoms based on individual variations (age, gender etc.), locations, time, environmental conditions, individual responses to disease (complete rest vs. working as usual), disease progress pattern, distribution of symptoms within a population, speed of disease spread across and within geographic areas etc. and 'back-track' these symptoms to the most probable causing agent, based on historical knowledge accumulated in the system.

g. When available, matching (1114) individuals' location and location history with causing agent to create a past and current mapping of location of causing agents in given areas h. Creating (1116) potential 'transmission pathways' based on users' location, population density and causing agents in a given area i. Defining (1118) the 'density' of causing agent in the population from above j. Correlating (1120) causing agent with particular sets of symptoms—note these sets of symptoms vary between demographic and other groups (such as infection history of individuals comprising the groups) and also vary with time/environmental conditions. E.g., symptoms of influenza infection in a given area in March may vary from symptoms of the same infection in December (based on weather, sequence variation, host status etc.).

k. For each diagnosis case, calculating (1122) the probability of a particular causing agent based on user past location, past infections (of user), symptoms and the various causing agent density in the areas visited by user on relevant time-scale (i.e., time that would match symptoms appearing at time t).

l. For each user—calculating (1124) the most probable "symptom course" (i.e., disease manifestation over time) based on population-wide symptoms for most probable causing agents and individual history of user, along with user-reported various details such as stress-level, exercise, hours of sleep etc. Stage 1124 may include creating "causing agent signature" based on the population "disease course" profiles and epidemic spread dynamics in area where the causing agent is known (via lab testing etc.)

m. Conveying (1126) to a user (or authorized health organization) the most probable causing agent and/or the likely disease course (in terms of symptoms) based on the above n. Detecting (1128) statistical anomalies in user symptoms requiring further medical attention and issue specific warnings to user and to caretaker/physician defining the nature of the anomaly o. Continuously updating (1130) disease course definition and statistical range as well as update causing agent density based on the addition of clinical data and/or users symptoms.

Stage 1102 may include:

1. Receiving Clinical reports from hospitals. Each report contains the data in table 1.

| ID * | Age | Gender | Date of hospitalization | Date of clinical test | Result of clinical test (pos/neg, causing agent) | Fever | Symptoms | Approximate address | Treatment | Outcome |
| --- | --- | --- | --- | --- | --- | --- | --- | --- | --- | --- |

2. Dividing area into geographic 'bins'. Size may vary. Bins will be identified and updated based on geographic disease clusters.

3. For each bin and for each causing agent identified—calculating the number of cases, % of causing agent out of total identified cases.

Data is summarized as in table 2. Table 2 includes the following columns:

| Bin # | # users | # positive | % positive of total | % positive of positive total | Symptoms (list) |
|---|---|---|---|---|---|

Stage 1104 may include:
1. From table 1 (above)—choosing each demographic group, e.g. 0-1 year old babies in the east Jerusalem area.
2. For each groups—organizing data by causing agent.
3. For each groups and causing agent pair—identify the distribution of symptoms, e.g. fever, throat, vomiting etc.
4. Summarize data as in table 3. Table 3 includes the following columns.

| Cluster # | Causing agent | Demographic group (list) | Symptom 1 (frequency, range) | Symptom 2 | Symptom 3 | Time (dates) |
|---|---|---|---|---|---|---|

Stage 1106 may include:
1. Allowing a mobile application (VT) hosted by a device of a user—to provide location information, sampling location information when VT is turned on or with every major location change.
2. Allowing users to use VT to fill in basic demographic info at registration (age, gender, family status, smoking etc.).
3. Allowing user to use VT to fill in basic symptoms (fever, vomiting, headache etc.).

Storing data from the VT reporting symptom and/or from HMOs/local MDs is stored as in table 4. Table 4 includes the following columns:

| User/ID from HMO | Demographic group (list) | Location | Symptom 1 (frequency, range) | Symptom 2 | Symptom 3 | Outcome |
|---|---|---|---|---|---|---|

Stage 1108 may include:
1. Mobile app (VT) allowing users to fill in symptoms daily
2. Gathering (by computerized system) daily data as in table 5 until disease is resolved.

Table 5 has the following columns:

| VT user ID | Demographic group (list) | Location | Date | Symptoms day 1 (list) | Symptoms day 2 (list) | Symptoms day 3 (list) etc. till disease is resolved | Outcome (e.g., resolved, medication, hospital etc.) |
|---|---|---|---|---|---|---|---|

3. Defining/creating (by computerized system) clusters of "disease course" based on the symptoms, demographics, length of infection, time and location. That is, similar symptoms from one connected area at a time consistent with infection chain (typically several weeks) will form a "disease course" for an area at a given time (table 6).

Table 6 has the following columns:

| Disease course group # | Demographic group (list) | Location | Typical symptoms by day (list, frequency, range) | Time (dates) | Typical outcome (e.g., resolved, medication, hospital etc.) |
|---|---|---|---|---|---|

4. Table 6 enables assigning new infection cases to a specific cluster based on location, time, demographics and symptoms.

5. Each cluster is associated with typical length of infection, typical symptoms and "complications" (e.g., if user had to go to hospital). The system can share this predictive info with new users reporting symptoms.

Stage 1110 may include:
Part 1—Danger Potential in Terms of Symptoms
1. Collecting (by computerized system) user symptoms via VT app.
2. Assigning (by computerized system) potential causing agent by assigning potential infectious agents to each cluster (pending clinical data).
3. Using (by computerized system) the following parameters to asses—the "danger potential" for each group: causing agent, outcome input from users in relevant disease course group and hospital outcome data
4. "danger potential" is an arbitrary definition and may be tuned. For example, a danger potential may be issued if a reporting user is in a group which has >X % chance of being hospitalized.

Part 2—Epidemic Potential
1. Collecting (by computerized system) user symptoms via VT app
2. Assigning (by computerized system) potential causing agent assigning potential infectious agents to each cluster (pending clinical data).
3. Comparing (by computerized system) speed of spread and symptoms from current epidemic to past data (same causing agent). If pattern and/or speed of spread and/or severity of symptoms are statistically greater than expected the system will issue warning to any relevant body Stage 1112 may include assigning potential infectious agents to each cluster (pending clinical data). This may include:

1. Combining (by computerized system) clustered clinical disease content data from hospitals (tables 2 and 3) and users disease course groups (table 6) based on location, time, symptoms, demographics and dynamics of causing agent in the population 2. For a given location/time—identifying (by computerized system) correlations between clusters (hospital) and symptom groups from users 3. Based on the correlations—assigning (by computerized system) to each disease course group a "probable causing agent" A correlation between clinical data clusters and disease course groups can involve taking into account (i) time when epidemic started in hospital (various nearby/connected locations) versus time when users started reporting, (ii) Demographics affected in hospital/among app users, and (iii) Typical symptoms and geographic distribution of infected.

Stage 116 may include:

1. Collecting (by computerized system) user symptoms/location via VT.

2. Organizing (by computerized system) on map the time-dependent pattern of user reports.

3. Using (by computerized system) users' location history to create a table of epidemiologically related individual users based on "Distance" (table 7).

Table 7 has the following columns:
User ID

| Interacting user ID | Distance** |
| --- | --- |

Wherein ** "Distance" is a function of physical distance between the two individuals (when at least one is infected/reporting symptoms) and the time spent at a relevant distance 4. Based on the above—attempting (by computerized system) to re-create the infection chain, where e.g. A user reports symptoms at time=t and was in proximity to another user at time t+1, after which second user reports symptoms then the "chain" is user 1 infected user 2

Stage 1142 may include:

1. Tracking (by computerized system) the geographic time-course of symptoms appearing in the population and define rate of geographic spread as well as 'disease course' groups.

3. Attempting (by computerized system) to find a pattern in the local spread, ignoring the noise that comes from entry of infected individuals into the area (which do not constitute an inherent part of the spread). A pattern consists of geographic spread rate, "disease course" profiles in the population and the relative abundance/order of each profile, e.g., first week we only see profile 1, after that a 50:50 mix of profile 1 and 2 etc.

It is noted that these signatures may require a positive identification of the causing agent in the area.

It is noted that if there are no clinical data the method can extrapolate potential causing agents based on causing agent signature, This may include:

1. Based on population symptoms in a given area at a given time—creating (by computerized system) 'disease course' groups as in table 6

2. Use existing disease course groups and the spatial dynamics of the epidemic to try and matching (by computerized system) those with the "causing agent signature" bank on the server (explained above, table 3).

3. Attaching (by computerized system) a "diagnosis" to the reported symptoms based on most similar causing agent signature.

Defining Local Disease Content and Symptoms at Time t

The system and method may first create (when possible) a list of causing agents at time t based on clinical reports from health organizations (MDs, HMOs, lab results, hospitals etc.). If there are no such data the system and method may extrapolate potential causing agents based on past data from the same area and from other regions where such data exists.

A list of causing agents may include of all relevant clinical data available, such as the exact strain and lineage of the causing agent (e.g., Influenza A H3N2, Fuji 2004, RNA sequence of viral genetic content etc.), clinical manifestations (headache, fever above 40 degrees, diarrhea etc. as well as length and timing of each symptom and symptom set as a whole), demographics (such as age, gender, location, socio-economic status when available, infection history when available etc.) and available medical notes.

Creating 'Symptom-Sets' Associated with a Particular Causing Agent at Time t.

The system and method may create a 'manifestation' table for each causing agent divided into clustered symptom sets associated with each discernible group infected, e.g., causing agent X infection in individuals of group Y is associated with symptom set and clinical outcome Z. Each such definition may be static or dynamic in time. That is, some causing agents (in some patient groups) may have symptoms that do not vary with time. For example, Ebola infection is always associated with hemorrhaging to some degree, so the system will define Ebola infection in ALL groups at ALL times as associated with hemorrhaging. This definition may change if and only if cases of Ebola not associated with such phenomena are reported, in which case the system will also attempt to define the 'difference' that caused the altered symptoms based on causing agent and/or infected population characteristics. On the other hand, some influenza infections lead to sore throat in some people while this symptom does not appear in other people, thus the system will attempt to find variations in causing agent, individuals infected and demographic and temporal factors responsible for the difference in symptoms. When such factors are found (in either of the above cases) a new infection/symptom group definition is created. For example, "Influenza infections in female children under the age of 7 (±2 years) during March 2012 are associated with sore throat".

Above symptom sets may be local or global as the system determines based on local and global clinical diagnosis and symptom reports.

"Functional mapping" of symptoms to identify causing agent with minimal lab testing The system will also create "functional mapping" of disease outcomes based on clinical symptom report over time with or without an associated causing agent definition. The system will again automatically cluster symptoms based on individual variations (age, gender etc.), locations, time, environmental conditions, individual responses to disease (complete rest vs. working as usual), disease progress pattern, distribution of symptoms within a population, speed of disease spread across and within geographic areas etc. and 'back-track' these symptoms to the most probable causing agent, based on historical knowledge accumulated in the system.

When a cluster of symptoms (cluster in terms of symptoms, demographics, spread dynamics and any of the parameters described above) cannot be associated with high degree of confidence with any particular causing agent due to any reason the system will create an alert and identify the users in the local network that are candidates for a positive disease identification via clinical sampling. That is, it will notify any health organization, hospital or private company interested that there is a disease pattern in a geographic area (either in real-time or retrospectively) that requires identification for causing agent.

Similarly, if/when a causing agent is identified for a disease the system will notify HMOs, hospital etc. that there is no further need for clinical testing at that particular time point for patients displaying symptoms as defined in the cluster. This recommendation will be based on statistical confidence and is only a money/labor-saving recommendation.

User Ad-Hoc Vaccination History and Statistical Determination of Cross-Immunity

Users' most likely infection history will be compiled via the VT application—after a user reports symptoms the system discovers (in real-time or retrospectively) the causing agent based on the steps described above.

The system attaches a "diagnosis" to the reported symptoms (which are kept on the server and/or on the users' device) including date of infection (start/end), severity of infection, probable causing agent (strain and specific mutations etc.). Next the system marks the user immune to specified causing agent and potentially closely related agents. To determine closeness the system will use all available scientific information regarding cross-immunity etc. as well system-generated statistical historical data showing the likelihood of infection B given infection A (when available). This way the system will define ad-hoc cross-immunities without experimental validation but based purely on population-wide infection history.

Note that given this vaccination history, cross-immunity and knowledge of circulating causing agents the system will update contagion probabilities for users. Furthermore, the system will be able to accurately suggest users to get vaccinated or not at a specific time, taking into account their own history, the vaccine strain and the circulating causing agent.

Also note that in some cases infection history may be verified and/or explored by consensual antibody analysis of users' blood and/or saliva, where the effectiveness of the user's immune system response against various causing agents will be tested, using standard methods (e.g., ELISA, HI assay etc.) These data may also be used in order to 'train' the system and enhance the knowledge database and analytics systems in use.

Population-Wide Warnings and Epidemic Tracking

The system is constantly attempting to attach symptom clusters to causing agents based on clinical and historical data. As mentioned above, the system defines "spread dynamics" to each causing agent, which serve as a "signature" for an infection, especially when no clinical data is available. As such, the system may cluster causing agents by the symptoms and disease pattern they produce. Using these causing agent clusters the system will automatically detect 'other' patterns that do not correspond to any known pattern (or combinations of patterns caused by several causing agents in one location). These 'other' patterns will then be used to define either a novel causing-agent, as in the case of rapidly emerging viruses such as the H1N1-pn strain, an environmental cause or a combination of both. As the causing agent is defined for these new patterns, e.g., via clinical testing, the pattern signature will be added to the database so that recurring episodes will be rapidly identified.

By using spread pattern signatures the system is able not only to identify existing diseases but also able to create disease pattern predictions based on the specific causing agent, environmental condition, demographics and the movement pattern of VT users. The result of these predictions for the end user (VT user or customers) is an accurate spatio-temporal map showing the most likely disease trajectories and the time it will take. These predictions will be frequently updated, as the exact individual movements within of the population cannot be predicted but must be taken into account Based on the above individual VT users will receive specific warnings when applicable (based on location, demographics, infection and movement history). Further, health organization may receive highly efficient vaccination/prevention strategies generated by the system. These will consist of highly targeted vaccination/prophylactic recommendations (e.g. provide vaccination against pertussis to kindergartens X, Y and Z) as well as other measures (quarantine etc.) if necessary. Note the reporting system features a 'built-in' prevention/containment strategy assessment capability—the degree of success of a strategy is reflected directly in the number of new cases in an area. Thus the system may be able to report success/failure in various locations automatically.

Indoor Monitoring of Persons Such as Patients

According to various embodiments of the invention the persons can be monitored when in door—in buildings, facilities, camps etc.

A hospital-based analysis system for identifying, tracking, containing and preventing hospital acquired infections. The system takes into account clinical test data from the hospital, patient-to-patient contacts, care giving staff and hospital floor plan, including the location of family rooms, WC, food areas etc.

This is an extension of all previous methods presented for the population level diagnosis, albeit applied to the settings of a facility. The system uses person-to-surface (surface may be a table, a syringe or a room etc.) and person-to-person contacts along with clinical test data and/or disease symptoms to create a transmission pathway and provide predictions on contaminated surfaces locations and potentially infected individuals.

The system first uses the floor plan to define the facility area. Patients and/or objects (medical equipment, office equipment etc.) may be marked with RFID tags or by any other device allowing tracking within the facility. Each RFID tag is associated with an object or patient ID. Active tracking of these RFID tags allows the system to superimpose object/individual location history using the ID, locations and time-stamps for each location. Each location can have a contact coefficient based on the nature of the location (i.e. WC versus TV room) and/or optimization of system based on past results. That is, the system may conclude that a location has a high contact coefficient based on the high incidence of transmission observed there.

For each potentially infected (including carrier) individual (or item) the system and method may calculate an epidemic distance (epi-distance) from all other IDs in the system (ID1, ID2, epi-distance) based on their interaction history (direct by sharing a location at the same time or indirect via sharing the same item or being in the same location at different times) and the known infections of each ID and/or potential infections determined by the system—for example, an ID closely associated with a carrier ID may be determined to likely become a carrier, even in the absence of clinical test results.

This embodiment may apply any of the above methods wherein the persons may be patient and the location information is gathered from a limited area.

FIG. 17 illustrates an indoor monitoring method 1700 according to an embodiment of the invention.

Creating (1710) a table of patients containing demographics (age, gender, general address etc.), reason for hospitalization (car accident, internal disease, operation etc.), location in hospital (ward, bed #), treatments received (antibiotics, drugs etc.), treatment/analysis rooms visited (MRI, CT etc.) and relevant clinical test results (i.e., tests for infectious agents, e.g. VRE, MRSA etc.). Note that patients may be assigned different "susceptibility" and/or "infectivity" potential to some or all diseases based on patient data (e.g., demographics). Patients are issued location-tracking devices such as RFID tags or other. Tags are associated with patient file from 1

Processing (1720) location data to create a list of locations visited including 'time stamps' containing time entered into location (t_entry) and time leaving the location (t_exit) (Table A).

Table A has the following columns:

| Patient ID | Location | Time (t_entry, t_exit) |
|---|---|---|

Calculating (1730) the epidemiological distance at any given time between two users. The epidemiological distance is defined by the patient-patient and patient-object tables (Tables B and C)—each location in the facility has a contact coefficient representing the likelihood of transmission in the area. For example, a kitchen area has higher probability for transmitting stomach infections than a TV room. Note these coefficients may be re-calculated as real data accumulates in the system by retrofitting parameters. The "Distance" is a value between 0 and 1, where a value of 0 is given for patients not in contact directly or indirectly and 1 indicates strongly related patients.

Table B has the following columns:

| Patient ID1 | Patient ID2 | Duration | Location contact coefficient | Distance |
|---|---|---|---|---|

Table C has the following columns:

| Patient ID | Object ID | Duration | Contact coefficient | Distance |
|---|---|---|---|---|

Creating (1740) a network of patients based on the pair-wise distances between patents. The network is highly dynamic and constantly updates based on movement data and contact with surfaces (table D). An example to surface contact is visitation to the same examination room for example.

Table D has the following columns:

| Patient ID1 | Patient ID2 | Distance (direct + indirect) |
|---|---|---|

Adding (1750) clinical data information to the network to establish potential disease paths as shown in table E (probable route is based on "distance", pathogen characteristics and patient infectivity/susceptibility status as defined in 1). Each pathogen has its own characteristics, such as latency period, transmission probability/location (based on transmission route) and object association (i.e., how easily the pathogen can last on surface and what probability of infection) as shown in table F.

Table E has the following columns:

| Patient ID1 (disease status) | Patient ID2 (disease status) | Distance | Transmission probability (based on patients' data) |
|---|---|---|---|

Table F has the following columns:

| Pathogen | Transmission chance/location | Latency | Symptoms | Surface contact |
|---|---|---|---|---|

Based on above—creating a summary for patient and object (location) potential status (table G and H).

Table G has the following columns:

| Patient ID | Causing agent 1 status (infected, suspected of infection (p), suspected of being carrier(p)) | Causing agent 2 status (infected, suspected of infection (p), suspected of being carrier(p)) | Etc. |
|---|---|---|---|

Table H has the following columns:

| Object/area ID | Causing agent 1 status (contaminated (p)) | Causing agent 2 status (contaminated (p)) | Etc. |
|---|---|---|---|

Figure 18:
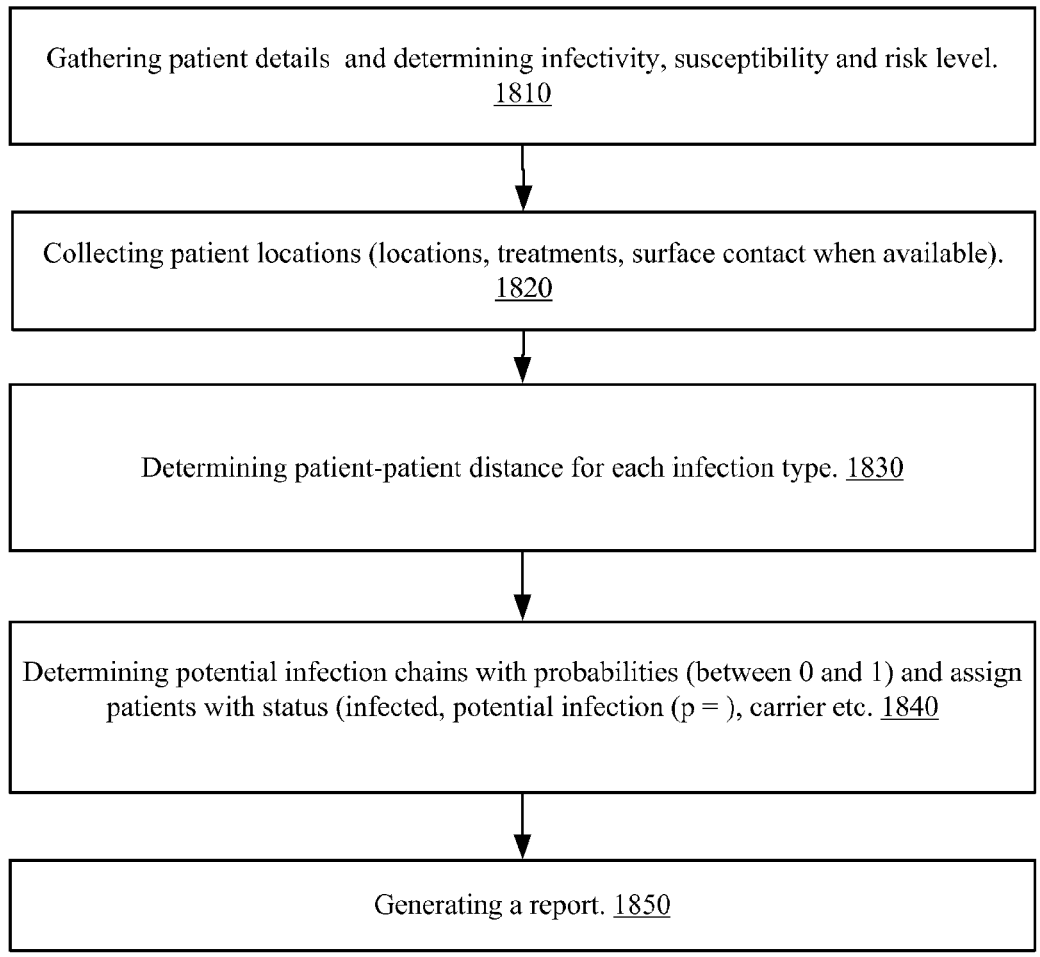
FIG. 18 illustrates a method according to an embodiment of the invention.

FIG. 18 illustrates method 1800 according to an embodiment of the invention.

Method 1800 may include: gathering (1810) patient details and determining infectivity, susceptibility and risk level; collecting (1820) patient locations (locations, treatments, surface contact when available); determining (1830) patient-patient distance for each infection type; determining (1840) potential infection chains with probabilities (between 0 and 1) and assign patients with status (infected, potential infection (p=), carrier etc; and generating (1850) a report.

Updating Patient Infectivity Data

According to yet another embodiment of the invention the method can includes defining ad-hoc cross-immunities without experimental validation but based purely on population-wide infection history.

Accordingly, the method may include at least some of the following stages:

Creating for each user of VT a table of putative infections based on location and demographics, reported (based on reported symptoms), and confirmed (with lab test results and/or MD opinion)

Creating clusters of users showing a similar infection history (in either putative, reported or confirmed), regardless of location and demographics Comparing the three clusters (each based on one column) and looks for groups of users that were putative but not reported or confirmed, creating a table (table I).

Table I has the following columns:
User ID Putative that did not get reported/confirmed (CA, date)

Calculating for patients in category, for each causing agent average, STD, CA that are statistically underrepresented in confirmed/reported vs. putative are organized in table J of users and the diseases they apparently did not contract.

Table J has the following columns:

| CA | STD from all CA | Users "not infected" |
|---|---|---|

For each CA in table J—creating create a table of users in group, including demographics and all (confirmed/reported) CA history Clustering the users according to CA or a combination of CA. The CA most associated with not being infected is a candidate for cross-immunity Checking likelihood of candidate CAs based on timing of infections—if the CA came after the CA by which the table was organized then it IS NOT causing cross-immunity. If 100% of users had first the candidate CA and then avoided the putative CA then likelihood is high.

Table K has the following columns:

| User ID | Demographics | CA 1 | CA 2 |
|---|---|---|---|

Creating a cross-immunity table (table L) based on results from the checking of likelihood.

Table L has the following columns:

| CA1 | CA2 (% immunity) |
|---|---|

FIG. 12 illustrates method 1200 according to an embodiment of the invention.

Method 1200 may include the following sequence of stages: determining (1210), by the computerized system, that a first person is infected by a first infectious disease; wherein the determination is associated with a first person infection probability attribute; detecting (1220), by the computerized system, based upon location information collected during at least a portion of a first infectious disease manifestation period and indicative of locations of the first persons and other persons, a second person that was within an infection distance from the first person and is potentially infected by the first infectious disease; calculating (1230), by the computerized system, a second person infection probability attribute; and updating (1240), by the computerized system, the first person infection probability attribute in response to the second person infection probability attribute.

These stages may be repeated for multiple uses and can be executed in an iterative and even recursive manner. In a nut shell—if it is confirmed (for example—by receiving clinical information that confirms that the first or second persons are infected by the first infectious disease then the probabilities are updated accordingly).

FIG. 13 illustrates method 1300 according to an embodiment of the invention.

Method 1300 may include the following sequence of stages: receiving (1310), by a computerized system, (a) location information relating to locations of multiple persons within a certain period of time; (b) clinical symptoms information related to one or more out of (a) at least one person of the multiple persons or (b) at least one of the locations; and evaluating (1320), by the computerized system, probabilities of infections of the multiple persons by at least one infectious disease, in response to the location information and to the clinical symptoms information.

Figure 14:
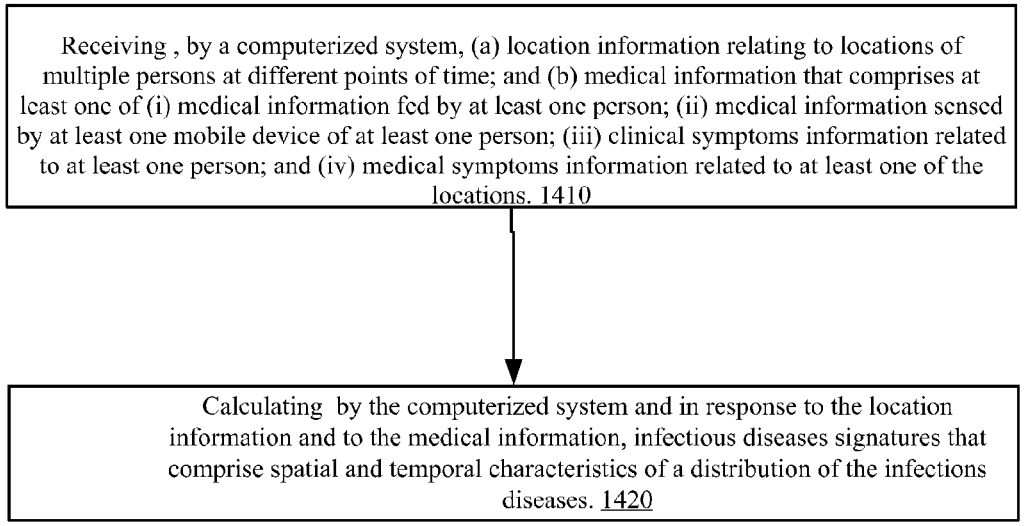
FIG. 14 illustrates a method according to an embodiment of the invention.

FIG. 14 illustrates method 1400 according to an embodiment of the invention.

Method 1400 may include the following sequence of stages: receiving (1410), by a computerized system, (a) location information relating to locations of multiple persons at different points of time; and (b) medical information that comprises at least one of (i) medical information fed by at least one person; (ii) medical information sensed by at least one mobile device of at least one person; (iii) clinical symptoms information related to at least one person; and (iv) medical symptoms information related to at least one of the locations; and calculating (1420) by the computerized system and in response to the location information and to the medical information, infectious diseases signatures that comprise spatial and temporal characteristics of a distribution of the infections diseases.

Figure 15:
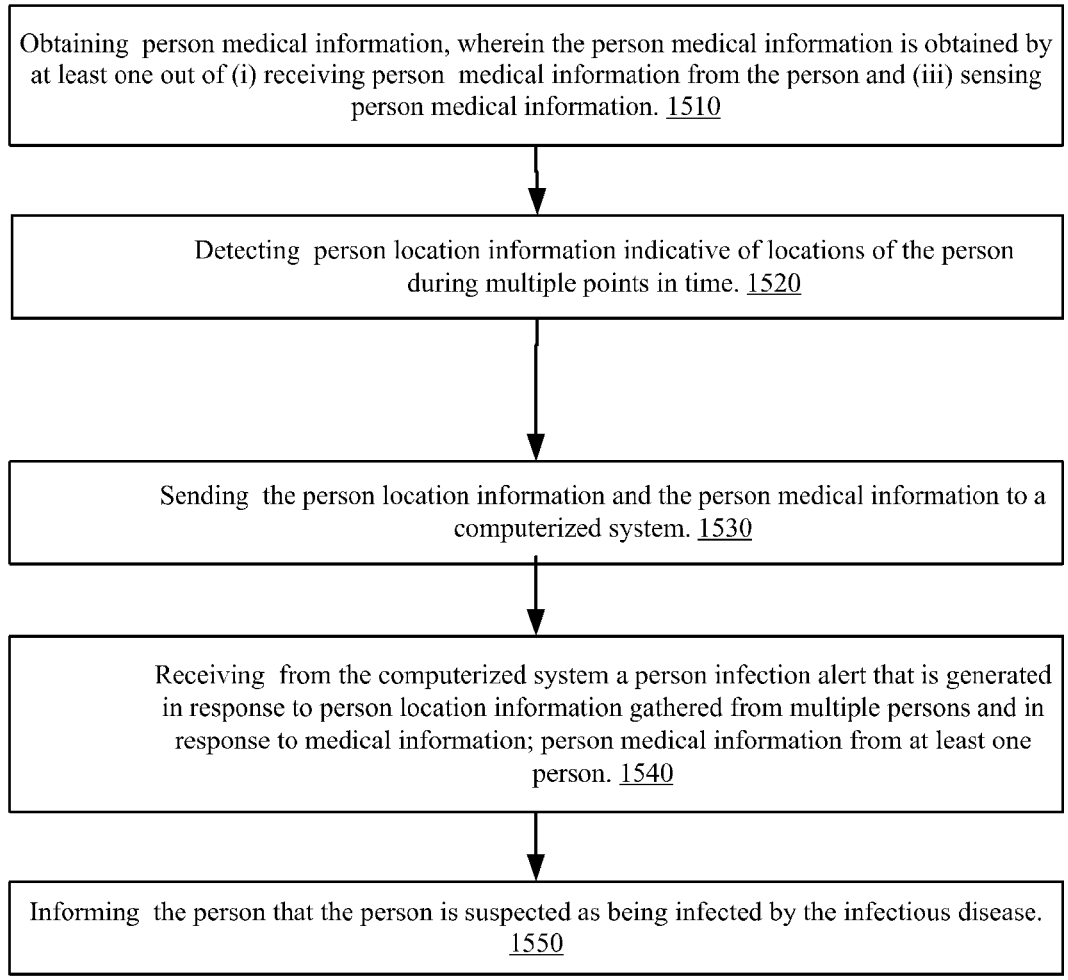
FIG. 15 illustrates a method according to an embodiment of the invention.

FIG. 15 illustrates method 1500 according to an embodiment of the invention.

Method 1500 may include the following sequence of stages: obtaining (1510) person medical information, wherein the person medical information is obtained by at least one out of (i) receiving person medical information from the person and (iii) sensing person medical information; detecting (1520) person location information indicative of locations of the person during multiple points in time; sending (1530) the person location information and the person medical information to a computerized system; receiving (1540) from the computerized system a person infection alert that is generated in response to person location information gathered from multiple persons and in response to medical information; person medical information from at least one person; and informing (1550) the person that the person is suspected as being infected by the infectious disease.

Figure 16:
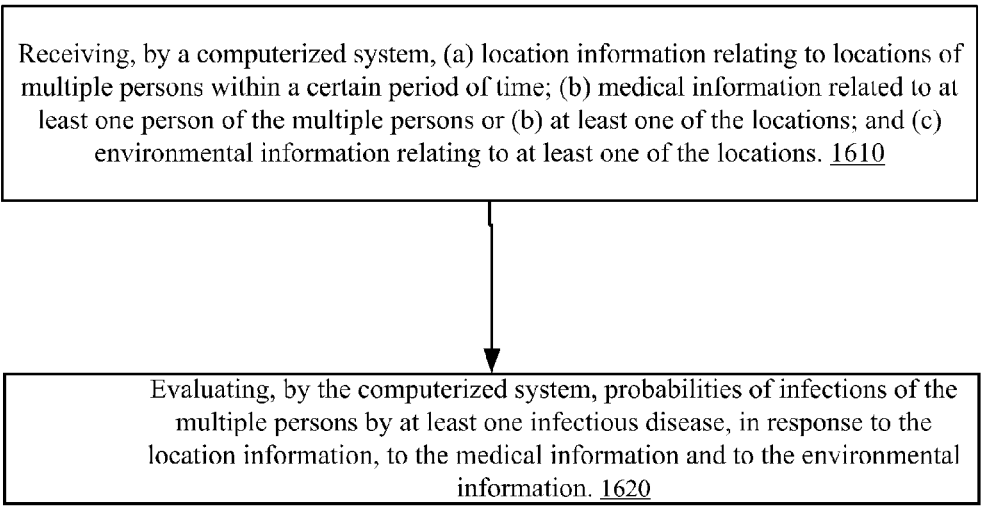
FIG. 16 illustrates a method according to an embodiment of the invention.

FIG. 16 illustrates method 1600 according to an embodiment of the invention.

Method 1600 may include the following sequence of stages: receiving (1610), by a computerized system, (a) location information relating to locations of multiple persons within a certain period of time; (b) medical information related to at least one person of the multiple persons or (b) at least one of the locations; and (c) environmental information relating to at least one of the locations; and evaluating (1620), by the computerized system, probabilities of infections of the multiple persons by at least one infectious disease, in response to the location information, to the medical information and to the environmental information.

The following examples include some tables that can be used in various methods mentioned above. It is noted that other data structures can be used.

FIG. 19 illustrates computerized system 20, multiple mobile devices 10, environmental sensors 12 and medical information source (such as a hospital) that is arranged to provide clinical information.

The mobile devices 10 can include sensors 12 and may host an application such as VT application 11.

The computerized system 20 can execute any of the methods mentioned above and may include various modules such as infection signature calculator 22 for calculating signatures of infectious diseases, location information processor 28 for calculating location information, distances between users and the like, the calculation may be responsive from location information provided from the user devices, clinical symptoms information processor 32, medical information module 24 for retrieving and processing medical information, probability calculator 26 for calculating probability attributes and any other statistical metadata, alert module 30 for generating alerts to specific users, to multiple users and to third parties.

According to an embodiment of the invention objects and/or places may be causes of infection. That is, when the proposal refers to a "person" it may also refer to an "object" or "location" which are suspect of being infectious. An example of an infectious object is a device used in a hospital (and is applicable mainly, if not only, to hospitals). An example of an infectious location may be a place of food (restaurant etc.) that is associated with people showing signs of infection after visiting the location, not necessarily at time when displaying symptoms. This way a contaminated food store may be traced for example. Again, it may be more relevant to hospitals, where a room may be contaminated for long periods of time and serve as a critical part of the infection chain—for example, a contaminated WC room in a hospital.

People infected may be infective without showing signs of disease (i.e., because of disease incubation period, because disease is still infectious after symptoms have ceased or because the disease is a-symptomatic (or nearly a-symptomatic) in the person, which may be quite common to some diseases. Thus the system may also "scan" for potential a-symptomatic carriers that spread the disease. These persons are treated quite similarly to infected locations, since neither shows symptoms . . . . The main difference is that these people are mobile, and thus instead of trying to correlate infection to a particular location the system may attempt to associate an a-symptomatic person's interaction to the symptoms he has come in contact with. For example, if I was a-symptomatic and met 5 people, 3 of which became infected not via any obvious infection chain, the system may mark me as an "a-symptomatic carrier" and notify me (or not).

The invention may also be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein can be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A non-transitory computer readable medium that stores instructions for causing a computerized system to perform the following operations:
   determining, by the computerized system, that a first person is infected by a first infectious disease; wherein the determination is associated with a first person infection probability attribute;
   detecting, by the computerized system, based upon location information collected during at least a portion of a first infectious disease manifestation period, the location information being indicative of locations of the first person and other persons, a second person that was within an infection distance from the first person and is potentially infected by the first infectious disease;
   calculating, by the computerized system, a second person infection probability attribute; and
   updating, by the computerized system, the first person infection probability attribute in response to the second person infection probability attribute;
   wherein at least one of the following is being held true:
   (i) the determining is responsive to at least one of (a) first person medical information fed by the first person, and (b) clinical information related to at least one of the first person and the first infectious disease;
   (ii) the determining is responsive to signatures of multiple infectious diseases;
   (iii) the location information is collected from hand held devices of the persons;
   (iv) the location information is collected from short-range transmission devices carried by the persons;
   (v) the determining and the calculating are responsive to demographic information relating to the first and second persons and to a demographic element of the signature of the first infectious disease;
   (vi) the determining and the calculating are responsive to demographic information relating to the first and second persons and to a demographic element of the signature of the first infectious disease and the non-transitory computer readable medium further stores instructions for updating, by the computerized system, the first person infection probability attribute and the second person infection probability attribute in response to clinical symptoms information relating to at least one of the first person, second person and the first infectious disease.

2. The non-transitory computer readable medium according to claim 1, wherein the determining is responsive to at least one of (a) first person medical information fed by the first person, and (b) clinical information related to at least one of the first person and the first infectious disease.

3. The non-transitory computer readable medium according to claim 1, wherein the determining is responsive to signatures of multiple infectious diseases.

4. The non-transitory computer readable medium according to claim 1, wherein the location information is collected from hand held devices of the persons.

5. The non-transitory computer readable medium according to claim 4, wherein the location information is collected from short-range transmission devices carried by the persons.

6. The non-transitory computer readable medium according to claim 4, wherein the location information is collected from long-range transmission devices carried by the persons.

7. The non-transitory computer readable medium according to claim 1, wherein the determining and the calculating are responsive to demographic information relating to the first and second persons and to the demographic element of the signature of the first infectious disease.

8. The non-transitory computer readable medium according to claim 1 that stores instructions for updating, by the computerized system, the first person infection probability attribute and the second person infection probability attribute in response to clinical symptoms information relating to at least one of the first person, second person and the first infectious disease.

9. A non-transitory computer readable medium that stores instructions for causing a computerized system to perform the following operations:
   receiving, by a computerized system, (a) location information relating to locations of multiple persons within a certain period of time; (b) clinical symptoms information related to one or more out of (a) at least one person of the multiple persons or (b) at least one of the locations;
   evaluating, by the computerized system, probabilities of infections of the multiple persons by at least one infectious disease, in response to the location information and to the clinical symptoms information; and
   wherein at least one of the following is being held true:
   (i) the non-transitory computer readable medium further stores instruction for generating a person infection alert if a probability of infection of the person by an infectious disease exceeds a first threshold; and for transmitting the person infection alert to at least the person;
   (ii) the non-transitory computer readable medium further stores instruction for generating a geographical zone infection alert if probabilities of at least a predefined number of persons that were, during the certain period of time, within the geographical infection alert exceed a second threshold; and for transmitting the geographical zone infection alert to a plurality of persons;
   (iii) the non-transitory computer readable medium further stores instruction for calculating infectious disease signatures in response to the location information and to the clinical symptoms information;
   (iv) the non-transitory computer readable medium further stores instruction for receiving by the computerized system, medical information provided by the persons; and wherein the evaluating, by the computerized system, of the probabilities of infections of the multiple persons is further responsive to medical information provided by the persons;
   (v) the non-transitory computer readable medium further stores instruction for receiving by the computerized system, medical information sensed by mobile devices of the multiple persons; and wherein the evaluating, by the computerized system, of the probabilities of infections of the multiple persons is further responsive to medical information provided by the persons;
   (vi) the non-transitory computer readable medium further stores instruction for receiving voice information sensed by mobile devices of the multiple persons; and processing the voice information to detect disease related voices;
   (vii) the non-transitory computer readable medium further stores instruction for calculating, by the computerized system, infections disease transmission pathways based upon the location information and the clinical symptoms information.

10. The non-transitory computer readable medium according to claim 9 that stores instructions for generating the person infection alert if the probability of infection of the person by the infectious disease exceeds the first threshold; and for transmitting the person infection alert to at least the person.

11. The non-transitory computer readable medium according to claim 9 that stores instructions for generating the geographical zone infection alert if probabilities of at least the predefined number of persons that were, during the certain period of time, within the geographical infection alert exceed the second threshold; and for transmitting the geographical zone infection alert to the plurality of persons.

12. The non-transitory computer readable medium according to claim 9 that stores instructions for calculating infectious disease signatures in response to the location information and to the clinical symptoms information.

13. The non-transitory computer readable medium according to claim 9 that stores instructions for receiving by the computerized system, medical information provided by the persons; and wherein the evaluating, by the computerized system, of the probabilities of infections of the multiple persons is further responsive to medical information provided by the persons.

14. The non-transitory computer readable medium according to claim 9 that stores instructions for receiving by the computerized system, medical information sensed by mobile devices of the multiple persons; and wherein the evaluating, by the computerized system, of the probabilities of infections of the multiple persons is further responsive to medical information provided by the persons.

15. The non-transitory computer readable medium according to claim 9 that stores instructions for receiving voice information sensed by mobile devices of the multiple persons; and processing the voice information to detect disease related voices.

16. The non-transitory computer readable medium according to claim 9 that stores instructions for calculating, by the computerized system, infections disease transmission pathways based upon the location information and the clinical symptoms information.

17. A non-transitory computer readable medium that stores instructions for causing a computerized system to perform the following operations:
   receiving, by a computerized system,
      (a) location information relating to locations of multiple persons at different points of time; and
      (b) medical information that comprises at least one of
         (i) medical information fed by at least one person;
         (ii) medical information sensed by at least one mobile device of at least one person;
         (iii) clinical symptoms information related to at least one person; and
         (iv) medical symptoms information related to at least one of the locations;
   calculating by the computerized system and in response to the location information and to the medical information, infectious diseases signatures that comprise spatial and temporal characteristics of a distribution of the infections diseases; and
   wherein at least one of the following is being held true:
   i) the non-transitory computer readable medium further stores instruction for evaluating, by the computerized system, probabilities of infections of the multiple persons by at least one infectious disease, in response to the location information and to the, infectious disease signatures;
   ii) the non-transitory computer readable medium further stores instruction for receiving by the computerized system demographic information related to at least one of the locations; and calculating by the computerized system and in response to the location information, the medical information and the demographic information, infectious diseases signatures that comprises environmental condition, spatial and temporal characteristics of the distribution of the infections diseases;

iii) the non-transitory computer readable medium further stores instruction for receiving by the computerized system environmental information related to the multiple locations persons; and calculating by the computerized system and in response to the location information, the medical information and the demographic information, infectious diseases signatures that comprise demographic, spatial and temporal characteristics of the distribution of the infections diseases.

18. The non-transitory computer readable medium according to claim 17 that stores instructions for evaluating, by the computerized system, probabilities of infections of the multiple persons by at least one infectious disease, in response to the location information and to the, infectious disease signatures.

19. The non-transitory computer readable medium according to claim 17 that stores instructions for receiving by the computerized system demographic information related to at least one of the locations; and calculating by the computerized system and in response to the location information, the medical information and the demographic information, infectious diseases signatures that comprises environmental condition, spatial and temporal characteristics of the distribution of the infections diseases.

20. The non-transitory computer readable medium according to claim 17 that stores instructions for receiving by the computerized system environmental information related to the multiple locations persons; and calculating by the computerized system and in response to the location information, the medical information and the demographic information, infectious diseases signatures that comprise demographic, spatial and temporal characteristics of the distribution of the infections diseases.

* * * * *